US010569076B2

(12) United States Patent
Kurihara et al.

(10) Patent No.: US 10,569,076 B2
(45) Date of Patent: Feb. 25, 2020

(54) VALVE AND FLUID CONTROL DEVICE

(71) Applicant: Murata Manufacturing Co., Ltd., Kyoto (JP)

(72) Inventors: Kiyoshi Kurihara, Kyoto (JP); Susumu Takeuchi, Kyoto (JP); Hiroaki Wada, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 438 days.

(21) Appl. No.: 15/632,843

(22) Filed: Jun. 26, 2017

(65) Prior Publication Data

US 2017/0292509 A1     Oct. 12, 2017

Related U.S. Application Data

(63) Continuation of application No. PCT/JP2015/086169, filed on Dec. 25, 2015.

(30) Foreign Application Priority Data

Dec. 26, 2014   (JP) .................................. 2014-264849

(51) Int. Cl.
  *A61M 39/22* (2006.01)
  *F16K 7/17* (2006.01)
  (Continued)

(52) U.S. Cl.
  CPC ............ *A61M 39/227* (2013.01); *A61M 1/06* (2013.01); *A61M 39/22* (2013.01);
  (Continued)

(58) Field of Classification Search
  CPC .. A61M 39/22; A61M 39/223; A61M 39/227; A61M 39/24; A61M 2039/242;
  (Continued)

(56) References Cited

U.S. PATENT DOCUMENTS

| 2005/0074662 A1 | 4/2005 | Cho |
| 2013/0178752 A1 | 7/2013 | Kodama |
| 2014/0031744 A1 | 1/2014 | Chen |

FOREIGN PATENT DOCUMENTS

| JP | H03-9764 A   | 1/1991 |
| JP | 2005-113918 A | 4/2005 |
| JP | 5185475 B2   | 4/2013 |

OTHER PUBLICATIONS

International Search Report issued in Application No. PCT/JP2015/086169 dated Mar. 15, 2016.
(Continued)

*Primary Examiner* — Shefali D Patel
(74) *Attorney, Agent, or Firm* — Pearne & Gordon LLP

(57) ABSTRACT

A fluid control device includes a piezoelectric pump, an inhaler, and a valve. The piezoelectric pump has a gas suction hole and a gas discharge hole. The inhaler has a container, an inhalation port, and a connection hole. The valve has a first ventilation hole, a second ventilation hole, a third ventilation hole, a first valve housing, a second valve housing, and a valve body. The first ventilation hole of the valve is connected to the connection hole of the inhaler. The second ventilation hole of the valve is connected to the suction hole of the piezoelectric pump. The third ventilation hole of the valve is opened to the atmosphere. The valve body is held between the first valve housing and the second valve housing, and configures a first region and a second region.

20 Claims, 29 Drawing Sheets

(51) Int. Cl.
- *F16K 17/164* (2006.01)
- *A61M 1/06* (2006.01)
- *F04B 53/10* (2006.01)
- *A61M 27/00* (2006.01)
- *F04B 17/03* (2006.01)
- *F04B 45/047* (2006.01)
- *F16K 11/02* (2006.01)
- *F04B 17/00* (2006.01)
- *F04B 43/04* (2006.01)
- *A61M 39/24* (2006.01)
- *B05B 11/00* (2006.01)
- *B05B 17/06* (2006.01)

(52) U.S. Cl.
CPC ......... *A61M 39/223* (2013.01); *F04B 53/103* (2013.01); *F16K 7/17* (2013.01); *F16K 17/164* (2013.01); *A61M 27/00* (2013.01); *A61M 2039/242* (2013.01); *B05B 11/00* (2013.01); *B05B 11/0005* (2013.01); *B05B 17/0607* (2013.01); *F04B 17/00* (2013.01); *F04B 17/003* (2013.01); *F04B 17/03* (2013.01); *F04B 43/04* (2013.01); *F04B 43/046* (2013.01); *F04B 45/047* (2013.01); *F16K 11/022* (2013.01)

(58) Field of Classification Search
CPC .. A61M 2039/2426; A61M 2039/2433; A61M 2039/2446; A61M 2039/246; A61M 2039/2493; A61M 1/06; F04B 53/10; F04B 53/102; F04B 53/103; F16K 7/12; F16K 7/14; F16K 7/17; F16K 11/02; F16K 11/022; F16K 15/14; F16K 15/144; F16K 15/147; F16K 17/02; F16K 17/025; F16K 17/164
See application file for complete search history.

(56) References Cited

OTHER PUBLICATIONS

Written Opinion issued in Application No. PCT/JP2015/086169 dated Mar. 15, 2016.

FIG. 4
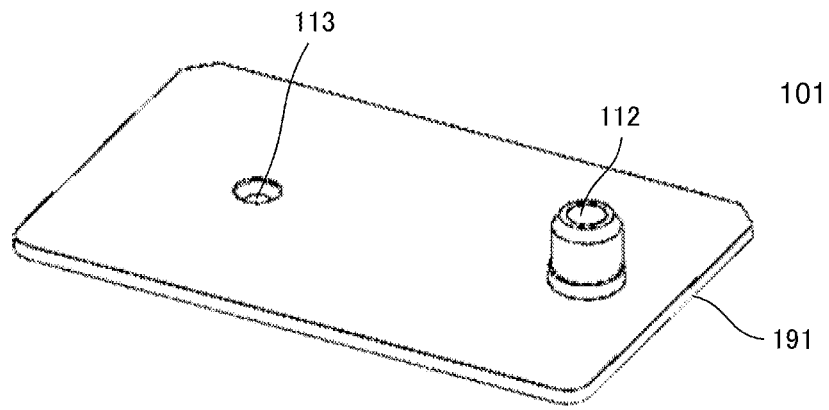
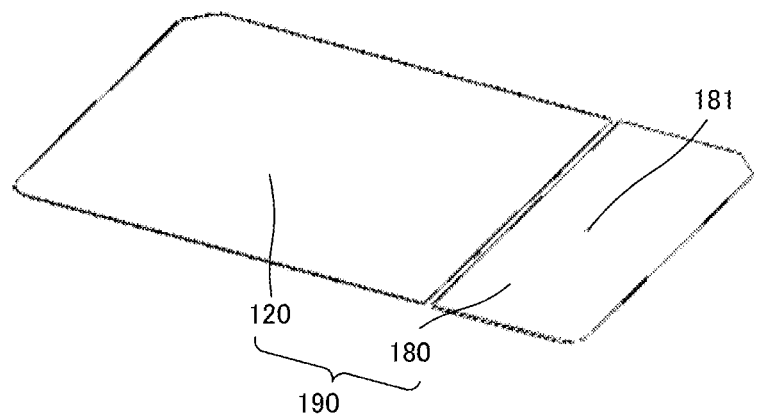
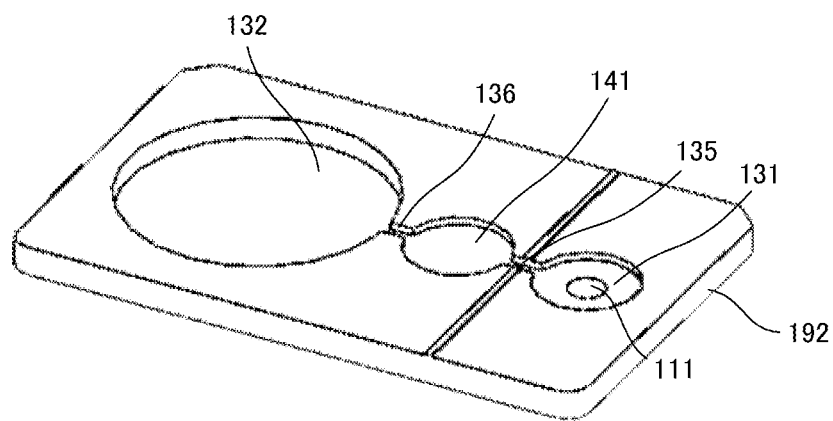

FIG. 5
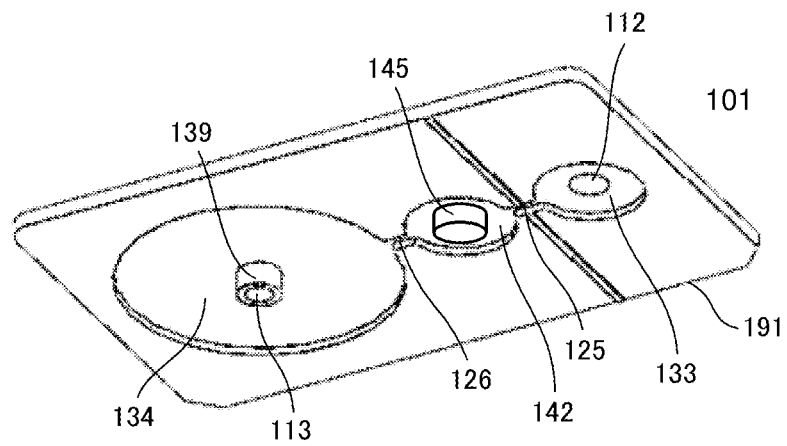
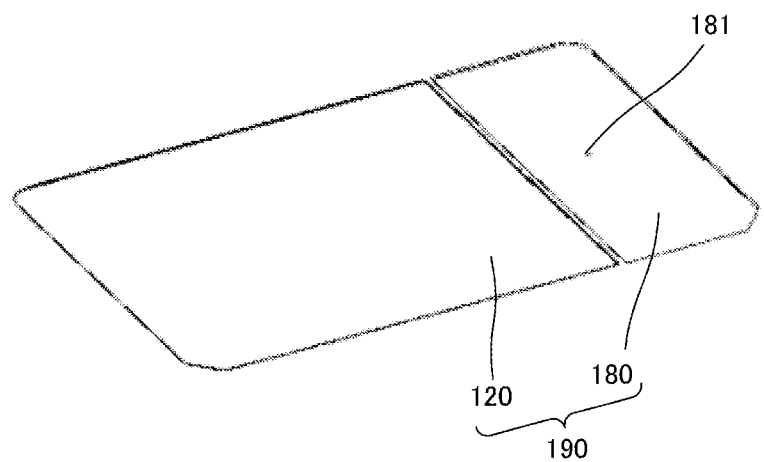
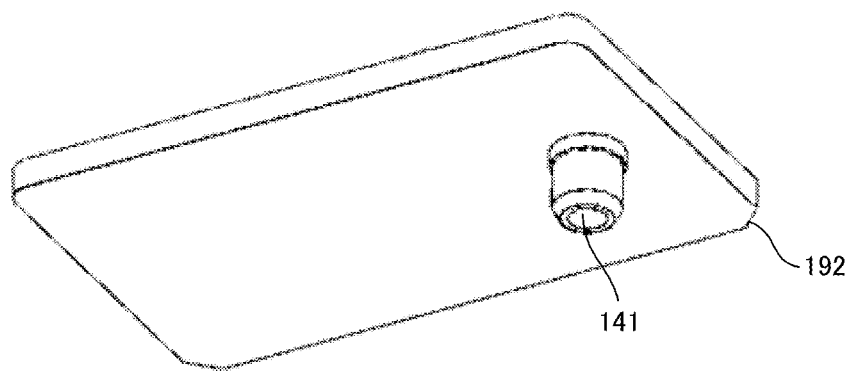

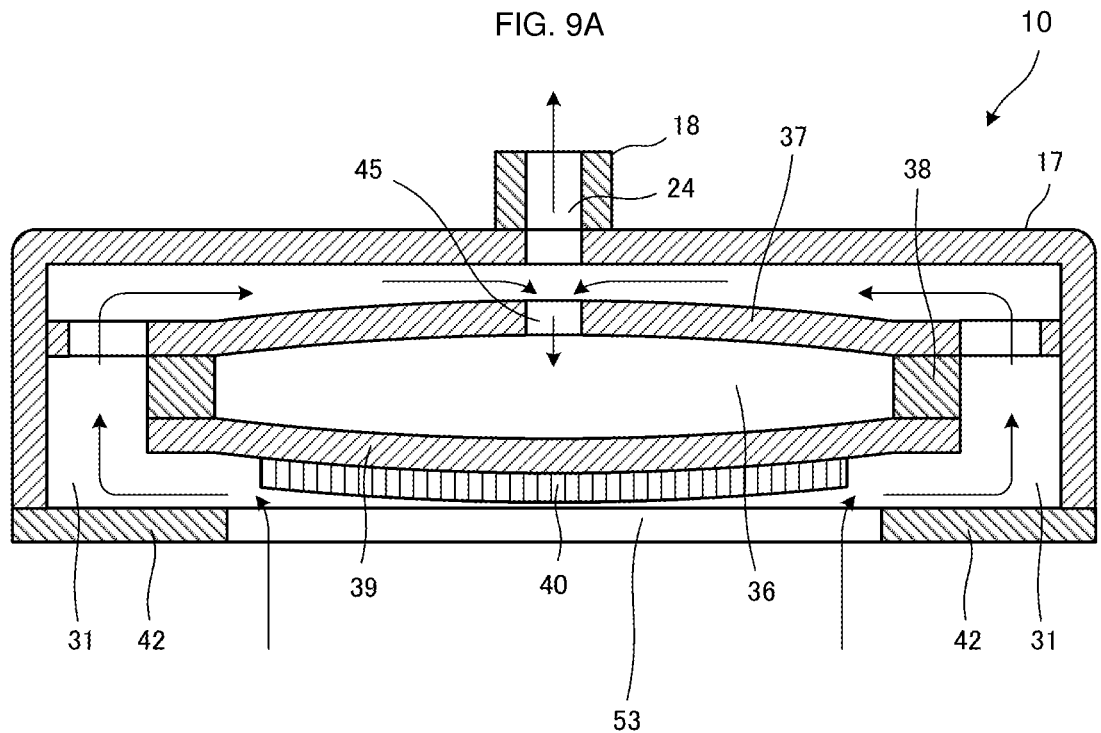
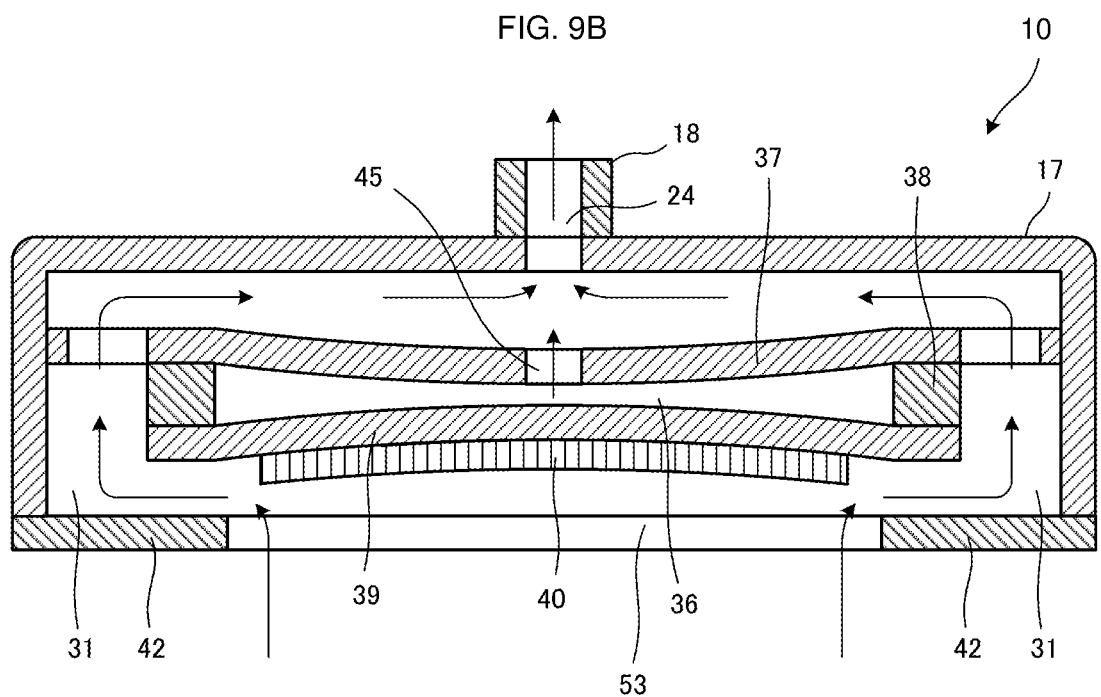

VALVE AND FLUID CONTROL DEVICE

This application is a continuation of International Application No. PCT/JP2015/086169 filed on Dec. 25, 2015 which claims priority from Japanese Patent Application No. 2014-264849 filed on Dec. 26, 2014. The contents of these applications are incorporated herein by reference in their entireties.

BACKGROUND OF THE DISCLOSURE

Field of the Disclosure

The present disclosure relates to a valve for switching a gas flow and a fluid control device including the valve.

Various types of existing fluid control devices controlling gas flow with valves have been devised. For example, Patent Document 1 discloses a fluid control device including a pump and a valve.

The pump has an air suction hole and an air discharge hole.

The valve includes a diaphragm, a first valve housing, and a second valve housing and has a configuration in which they are laminated in order. Furthermore, a ventilation hole, an exhaust port, and a cuff connection port are provided in the valve. The discharge hole of the pump is connected to the ventilation hole. The exhaust port is opened to the atmosphere.

The diaphragm of the valve closes or opens the exhaust port based on a difference between pressures that are applied to both the surfaces of the diaphragm. An arm band rubber tube of a cuff is connected to the cuff connection port of the valve to cause the fluid control device to be connected to the cuff.

With the above-described configuration, the fluid control device disclosed in Patent Document 1 drives the pump, and discharges the air into the valve from the discharge hole of the pump. The diaphragm closes the exhaust port with a pressure of the air discharged into the valve. Therefore, the air discharged into the valve flows into the cuff from the cuff connection port. With this, the fluid control device disclosed in Patent Document 1 fills the cuff with compressed air.

Thereafter, when driving of the pump is stopped, the diaphragm opens the exhaust port with the pressure of the cuff. The compressed air in the cuff is therefore exhausted from the exhaust port. Thus, the valve in Patent Document 1 can passively release the pressure in the cuff (flow path) to the atmosphere.

Patent Document 1: Japanese Patent No. 5185475

BRIEF SUMMARY OF THE DISCLOSURE

However, the valve in Patent Document 1 does not perform a suction operation of sucking gas from the inside of a container and making the inside of the container be at a negative pressure.

Meanwhile, there is a suction device that sucks fluid such as body fluid and the air into a container from the body of a patient with a tube (flow path) inserted into the body interposed therebetween. The suction device has a problem that the tube is closed when an inhalation port of the tube makes close contact with a tissue in the body during the suction. In order to avoid this problem, the suction device has a safety function of detecting a tube-closed state using a pressure sensor and a flowmeter and actively releasing the pressure in the tube (flow path) to the atmosphere using an electromagnetic valve or the like.

However, components such as the pressure sensor, the flowmeter, and the electromagnetic valve are needed in order to provide this safety function. The existing suction device therefore has a problem that a device main body is increased in size and cost.

An object of the present disclosure is to provide a valve that can perform a fluid suction operation and can passively release the pressure in a flow path to the atmosphere, and a fluid control device including the valve.

A valve according to an aspect of the present disclosure has the following configuration in order to achieve the above-described object.

(1) The valve includes:

a valve housing that has a first ventilation hole, a second ventilation hole, and a third ventilation hole; and a valve body that configures a first region communicating with the first ventilation hole and a second region communicating with the second ventilation hole in the valve housing, wherein the valve body has a fixed portion with a first through-hole communicating the first region and the second region with each other and a movable portion switching a communication state between the second ventilation hole and the third ventilation hole, the valve body is fixed to the valve housing such that:

when a pressure in the first region is higher than a pressure in the second region, the valve body blocks communication between the second ventilation hole and the third ventilation hole and communicates the first ventilation hole and the second ventilation hole with each other with the first through-hole interposed therebetween, and when the pressure in the first region is equal to or lower than the pressure in the second region, the valve body communicates the second ventilation hole and the third ventilation hole with each other and communicates the first ventilation hole and the second ventilation hole with each other with the first through-hole interposed therebetween.

With this configuration, for example, an inhaler having an inhalation port is connected to the first ventilation hole, a suction hole of a pump is connected to the second ventilation hole, and the third ventilation hole is opened to the atmosphere. In this case, when the pump is driven, the air in the second region is sucked into the pump while passing through the second ventilation hole and the suction hole. Then, the air in the pump is discharged from a discharge hole.

In the fixed portion of the valve body, although the first region and the second region communicate with each other with the first through-hole interposed therebetween, pressure loss (flow path resistance) is generated with the first through-hole. For this reason, in the valve, the pressure in the first region is higher than the pressure in the second region.

Accordingly, the movable portion can close the third ventilation hole using a pressure difference between the first region and the second region to block communication between the second ventilation hole and the third ventilation hole.

The valve having this configuration causes the air to flow to the second ventilation hole from the first ventilation hole while passing through the first through-hole when the pressure in the first region is higher than the pressure in the second region.

As a result, gas in a container of the inhaler is discharged to the first region of the valve while passing through the first ventilation hole, and is sucked into the pump while passing through the second ventilation hole and the suction hole. With this suction, a pressure (pressure of the gas) in the container becomes lower than the atmospheric pressure and is a negative pressure. Therefore, the inhaler can inhale liquid (for example, breast milk, blood, pleural effusion, sputum, or the like) at the outside of the container into the container from the inhalation port.

Then, when driving of the pump is stopped, the pressure in the container reaches a maximum suction pressure of the pump, or a flow path such as a tube is closed, the pressure in the first region becomes equal to the pressure in the second region with the first through-hole. It should be noted that the pressure in the first region and the pressure in the second region at this time are equal to or lower than the atmospheric pressure.

Therefore, the movable portion can open the third ventilation hole using the atmospheric pressure to communicate the second ventilation hole and the third ventilation hole with each other.

With this, the air flows to the first ventilation hole from the third ventilation hole while passing through the first through-hole. Thereafter, the air flowed out from the first ventilation hole flows into the container while passing through the tube. The pressure (air pressure) in the container is thereby increased to return to the atmospheric pressure.

Accordingly, the valve having this configuration can perform a fluid suction operation and can passively release the pressure in the flow path to the atmosphere.

(2) It is preferable that the movable portion make contact with or be separated from a first portion as a part of the valve housing with a pressure difference between the first region and the second region to switch the communication state.

With this configuration, when the pressure in the first region is higher than the pressure in the second region, the movable portion makes contact with the first portion of the valve housing to block communication between the second ventilation hole and the third ventilation hole.

On the other hand, when the pressure in the first region is equal to or lower than the pressure in the second region, the movable portion is separated from the first portion of the valve housing to communicate the second ventilation hole and the third ventilation hole with each other.

(3) It is preferable that the valve housing have, in the first portion, the third ventilation hole and a valve seat projecting to the movable portion side from a circumference of the third ventilation hole in the second region, and the valve body be fixed to the valve housing such that the movable portion makes contact with the valve seat.

With this configuration, when the pressure in the first region is higher than the pressure in the second region, the movable portion makes contact with the valve seat to block communication between the second ventilation hole and the third ventilation hole.

On the other hand, when the pressure in the first region is equal to or lower than the pressure in the second region, the movable portion is separated from the valve seat to communicate the second ventilation hole and the third ventilation hole with each other.

(4) It is preferable that the movable portion have a second through-hole communicating the first region and the second region with each other when the second ventilation hole communicates with the first ventilation hole and the third ventilation hole.

(5) It is preferable that the movable portion make contact with or be separated from a second portion as a part of the valve housing to close or open the second through-hole, and the valve body be fixed to the valve housing such that:

when the pressure in the first region is higher than the pressure in the second region, the valve body closes the second through-hole, and when the pressure in the first region is equal to or lower than the pressure in the second region, the valve body opens the second through-hole to communicate the first ventilation hole, the second ventilation hole, and the third ventilation hole with each other with the first through-hole and the second through-hole interposed therebetween.

With this configuration, when the pressure in the first region is higher than the pressure in the second region, the movable portion makes contact with the second portion of the valve housing to close the second through-hole.

On the other hand, when the pressure in the first region is equal to or lower than the pressure in the second region, the movable portion is separated from the second portion of the valve housing to open the second through-hole. In this case, the air flows to the first ventilation hole from the third ventilation hole while passing through the second through-hole.

That is to say, with this configuration, the air flows to the first ventilation hole from the third ventilation hole while passing through both the first through-hole and the second through-hole.

As a result, the air rapidly flows into the container from the third ventilation hole. The pressure (air pressure) in the container is thereby increased to rapidly return to the atmospheric pressure.

Accordingly, the valve having this configuration can passively release the pressure in the flow path to the atmosphere for a short time.

(6) It is preferable that the valve housing have a fourth ventilation hole communicating with the first region.

The valve having this configuration can maintain a decompressed state of the container while the pump is continuously driven.

(7) It is preferable that a cross-sectional area of the fourth ventilation hole be smaller than a cross-sectional area of the first ventilation hole.

(8) It is preferable that a cross-sectional area of the fourth ventilation hole be larger than a cross-sectional area of the first through-hole.

(9) It is preferable that the valve housing have a filter which passes gas and prevents liquid from passing.

With the valve having this configuration, when liquid adheres to the filter at the time of suction to increase ventilation resistance of the filter, the pressure difference between the first region and the second region is eliminated and the movable portion opens the third ventilation hole. The atmospheric release generates a sound when the air passes therethrough.

Accordingly, this configuration enables a nurse or other staff to easily detect clogging of the filter with the sound in the atmosphere release.

Furthermore, a fluid control device according to another aspect of the disclosure has the following configuration in order to achieve the above-described object.

(10) The fluid control device includes:

the valve according to any one of the above-described aspects (1) to (9);

a pump having a suction hole and sucking gas from the suction hole; and an inhaler having a inhalation port for inhaling fluid, wherein the first ventilation hole of the valve communicates with a part of the inhaler, and the second ventilation hole of the valve communicates with the suction hole of the pump.

With this configuration, the usage of the valve according to any one of the above-described aspects (1) to (9) enables the fluid control device including the valve to provide the same effects.

(11) It is preferable that the inhaler inhale the breast milk from the inhalation port.

With this configuration, the fluid control device is used as a breast pump. The breast milk inhaled from the inhalation port is stored in the container.

(12) It is preferable that the inhaler have:

a first container which is connected to the inhalation port and stores liquid inhaled from the inhalation port;

a second container which is connected to the first container and passes gas and prevents passing of liquid; and a third container which is connected to the second container and the suction hole of the pump, and adjusts a suction pressure of the gas which is sucked by the pump.

With this configuration, the fluid control device is used as a drainage. Blood, pleural effusion, or the like inhaled from the inhalation port is stored in the first container.

The present disclosure can perform a fluid suction operation and can passively release the pressure in a flow path to the atmosphere.

BRIEF DESCRIPTION OF THE SEVERAL VIEWS OF THE DRAWINGS

FIG. 4 is an exploded perspective view of the valve 101 illustrated in FIG. 1.

FIG. 5 is an exploded perspective view of the valve 101 illustrated in FIG. 1.

FIGS. 9A and 9B are cross-sectional views of the piezoelectric pump 10 illustrated in FIG. 6 cut along the line S-S when the piezoelectric pump 10 is operated in a primary mode. FIG. 9A is a view when a volume of a pump chamber is increased and FIG. 9B is a view when the volume of the pump chamber is reduced.

DETAILED DESCRIPTION OF THE DISCLOSURE

Hereinafter, a fluid control device 100 according to a first embodiment of the disclosure will be described.

Figure 1:
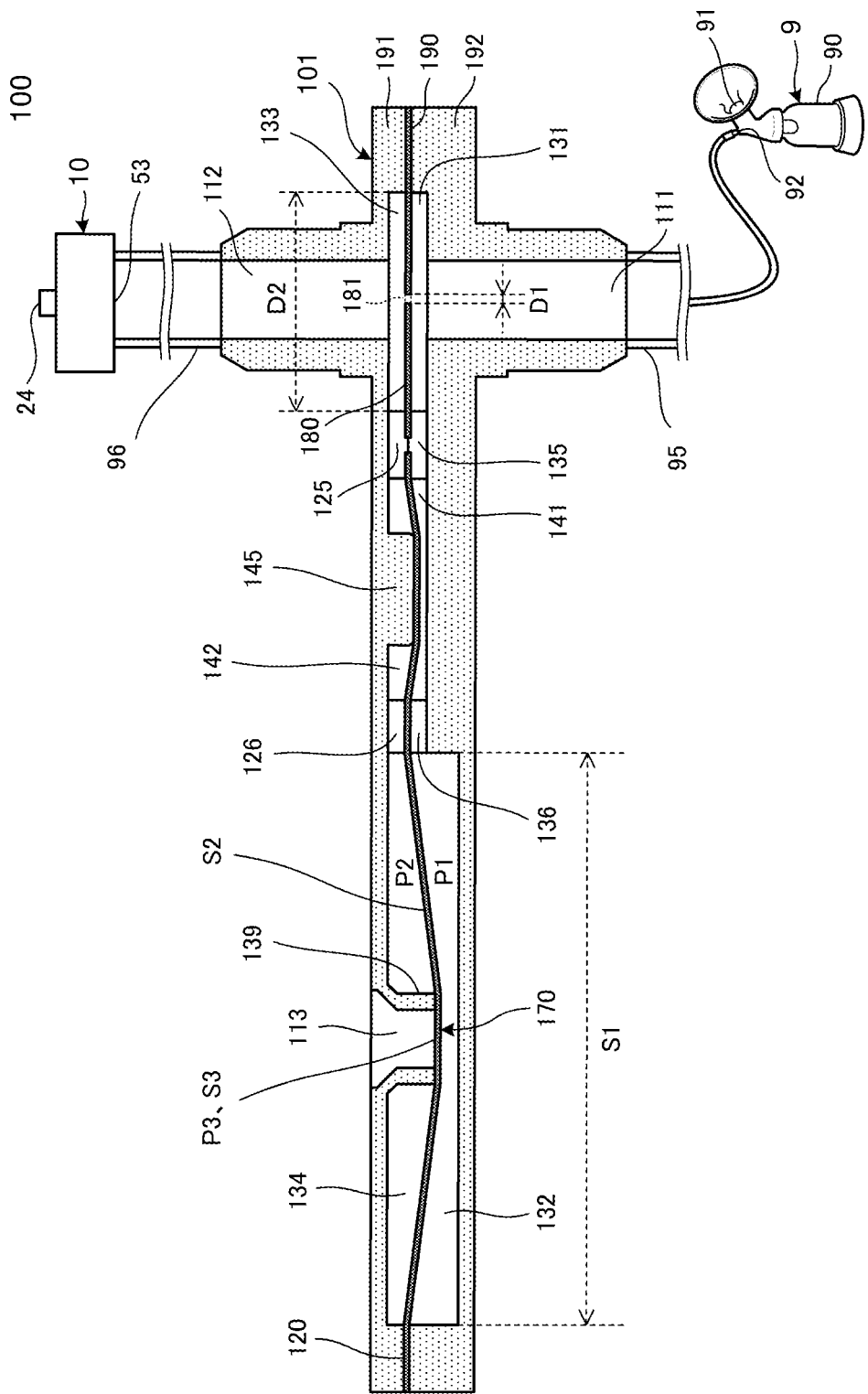
FIG. 1 is a cross-sectional view of a fluid control device 100 according to a first embodiment of the disclosure.

FIG. 1 is a cross-sectional view of the fluid control device 100 according to the first embodiment of the disclosure. The fluid control device 100 includes a piezoelectric pump 10, an inhaler 9, and a valve 101. The fluid control device 100 is a device that sucks liquid (for example, breast milk or the like). The valve 101 illustrated in FIG. 1 corresponds to a cross section along a line T-T illustrated in FIG. 2, which will be described later.

The piezoelectric pump 10 has a suction hole 53 for sucking gas and a discharge hole 24 for discharging the gas as details thereof will be described later.

The inhaler 9 has a container 90, an inhalation port 91, and a connection hole 92. The inhaler 9 is, for example, a breast pump. The inhalation port 91 is attached to, for example, the breast of a human being or an animal. The container 90 stores therein the liquid (for example, breast milk or the like).

The valve 101 has a first ventilation hole 111, a second ventilation hole 112, and a third ventilation hole 113 as details thereof will be described later. The first ventilation hole 111 of the valve 101 is connected to the connection hole 92 of the inhaler 9. The second ventilation hole 112 of the valve 101 is connected to the suction hole 53 of the piezoelectric pump 10. The third ventilation hole 113 of the valve 101 is opened to the atmosphere.

It should be noted that in FIG. 1, the first ventilation hole 111 of the valve 101 and the connection hole 92 of the inhaler 9 are connected to each other with a tube 95 interposed therebetween. In the same manner, in FIG. 1, the second ventilation hole 112 of the valve 101 and the suction hole 53 of the piezoelectric pump 10 are also connected to each other with a tube 96 interposed therebetween. It may be sufficient that these connections are achieved by employing any connection method in the implementation.

Next, the configurations of the valve 101 and the piezoelectric pump 10 will be described in detail. First, the configuration of the valve 101 will be described in detail with reference to FIG. 1 to FIG. 5.

Figure 2:
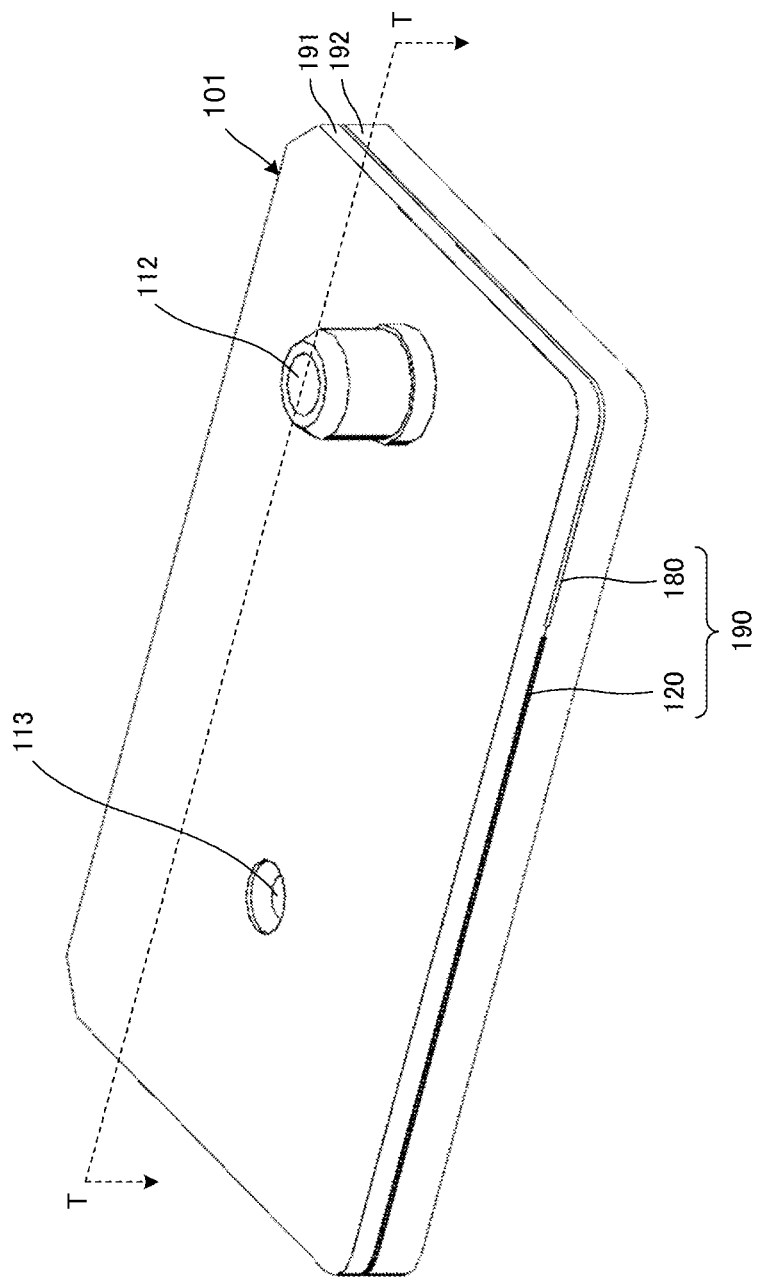
FIG. 2 is an outer appearance perspective view of a valve 101 illustrated in FIG. 1.
Figure 3:
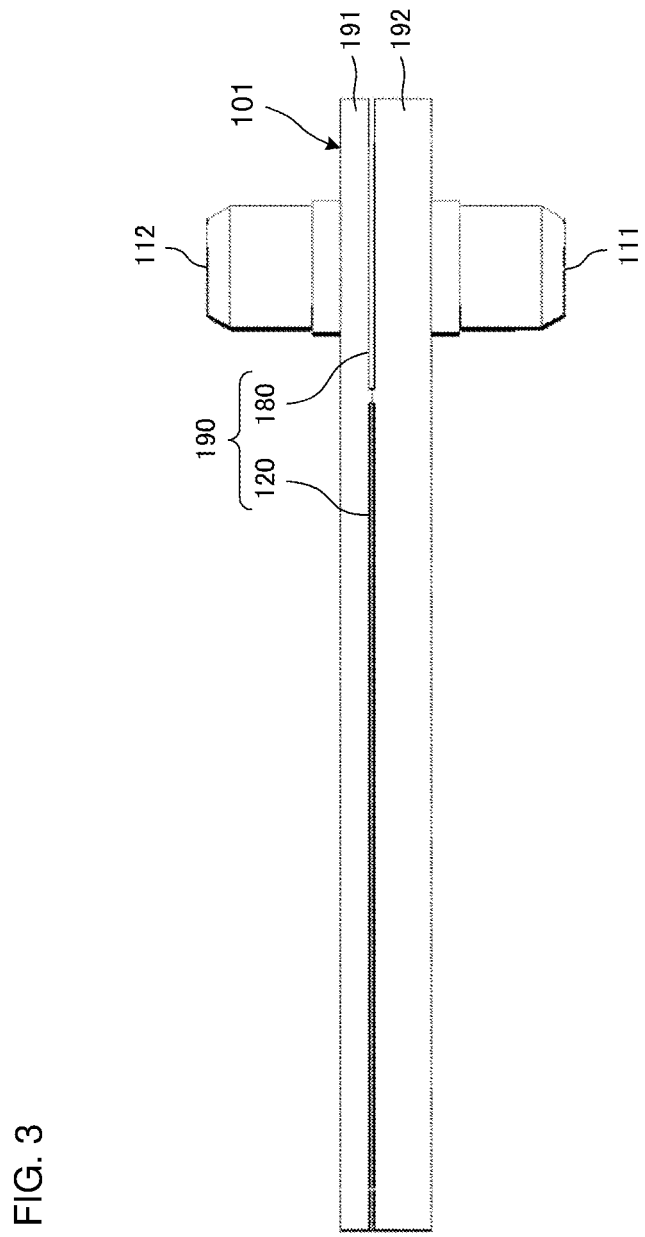
FIG. 3 is a side view of the valve 101 illustrated in FIG. 1.

FIG. 2 is an outer appearance perspective view of the valve 101 illustrated in FIG. 1. FIG. 3 is a side view of the valve 101 illustrated in FIG. 1. FIG. 4 and FIG. 5 are exploded perspective views of the valve 101 illustrated in FIG. 1. FIG. 4 is the exploded perspective view when the valve 101 is seen from the upper surface side and FIG. 5 is the exploded perspective view when the valve 101 is seen from the bottom surface side.

As illustrated in FIG. 2 to FIG. 5, the valve 101 includes a second valve housing 192, a valve body 190, and a first valve housing 191 and has the configuration in which they are laminated in order.

As illustrated in FIG. 1 to FIG. 5, the first valve housing 191 has the second ventilation hole 112 communicating with the suction hole 53 of the piezoelectric pump 10, the third ventilation hole 113 communicating with the outside of the fluid control device 100, a valve seat 139 projecting to the valve body 190 side from the circumference of the third ventilation hole 113, a columnar valve seat 145 projecting to the valve body 190 side, a communication path 125 communicating a second upper valve chamber 142 and a first upper valve chamber 133 with each other, and a communication path 126 communicating the second upper valve chamber 142 and a third upper valve chamber 134. The first valve housing 191 is made of, for example, resin. The valve seat 139 is formed to have a columnar shape having the third ventilation hole 113 in a center portion.

It should be noted that the first valve housing 191 has the valve seat 145, but is not required to have it. The second upper valve chamber 142 and a second lower valve chamber 141 are not required to be necessarily included. It is sufficient that the communication path 125 and the communication path 126 communicate with each other and a communication path 135 and a communication path 136 communicate with each other.

As illustrated in FIG. 1 to FIG. 5, the second valve housing 192 has the first ventilation hole 111 communicating with the connection hole 92 of the inhaler 9, the communication path 135 communicating the second lower valve chamber 141 and a first lower valve chamber 131 with each other, and the communication path 136 communicating the second lower valve chamber 141 and a third lower valve chamber 132 with each other. The second valve housing 192 is made of, for example, resin.

The valve body 190 has a fixed portion 180 and a movable portion 120. The fixed portion 180 is made of, for example, resin. The movable portion 120 is configured by a rectangular diaphragm. A material of the movable portion 120 is, for example, rubber such as ethylene propylene diene rubber (EPDM) and silicone. The fixed portion 180 and the movable portion 120 are made to adhere to each other with an adhesive or the like.

A circular first through-hole 181 is provided in a center portion of a region of the fixed portion 180, which makes contact with the first upper valve chamber 133 and the first lower valve chamber 131, as illustrated in FIG. 1 to FIG. 5. The first through-hole 181 communicates the first upper valve chamber 133 and the first lower valve chamber 131 with each other.

The valve body 190 is held between the first valve housing 191 and the second valve housing 192 with, for example, a double-sided tape, an adhesive, or the like interposed therebetween.

As illustrated in FIG. 1, the valve body 190 is fixed to the first valve housing 191 and the second valve housing 192 such that a part of the movable portion 120 makes contact with the valve seats 139 and 145.

The valve body 190 is fixed to the first valve housing 191 and the second valve housing 192, thereby dividing inside the first valve housing 191 and the second valve housing 192.

Thus, as illustrated in FIG. 1 to FIG. 5, the valve body 190 configures, in the first valve housing 191 and the second valve housing 192, the columnar first lower valve chamber 131, the columnar second lower valve chamber 141, the columnar third lower valve chamber 132, the columnar first upper valve chamber 133, the annular ring-shaped second upper valve chamber 142, and the annular ring-shaped third upper valve chamber 134.

The first lower valve chamber 131 communicates with the first ventilation hole 111. The first lower valve chamber 131 communicates with the second lower valve chamber 141 with the communication path 135 interposed therebetween. The third lower valve chamber 132 communicates with the second lower valve chamber 141 with the communication path 136 interposed therebetween.

Furthermore, the first upper valve chamber 133 communicates with the second ventilation hole 112. The first upper valve chamber 133 communicates with the second upper valve chamber 142 with the communication path 125 interposed therebetween. The third upper valve chamber 134 communicates with the second upper valve chamber 142 with the communication path 126 interposed therebetween.

It should be noted that the first lower valve chamber 131, the communication path 135, the second lower valve chamber 141, the communication path 136, and the third lower valve chamber 132 correspond to an example of a "first region" according to the disclosure. The first upper valve chamber 133, the communication path 125, the second upper valve chamber 142, the communication path 126, and the third upper valve chamber 134 correspond to an example of a "second region" according to the disclosure. The valve seat 139 corresponds to an example of a "valve seat" according to the disclosure.

As illustrated in FIG. 1, the valve body 190 configures an exhaust valve 170 together with the first valve housing 191 and the second valve housing 192. The exhaust valve 170 is configured by the third lower valve chamber 132, the third upper valve chamber 134, the valve seat 139, and a region of the valve body 190, which faces the third lower valve chamber 132 and the third upper valve chamber 134.

As illustrated in FIG. 1, in the exhaust valve 170, the movable portion 120 of the valve body 190 is made into the following state when the area of a portion of the valve body 190, which faces the third lower valve chamber 132, is S1, a pressure in the third lower valve chamber 132 is P1, the area of a portion of the valve body 190, which faces the third upper valve chamber 134, is S2, a pressure in the third upper valve chamber 134 is P2, the area of a portion of the valve body 190, which faces the third ventilation hole 113, is S3, and a pressure in the third ventilation hole 113 (atmospheric pressure in the embodiment), is P3.

That is to say, when a relation of S1×(P1−P2)>S3×(P3−P1) is satisfied, the movable portion 120 makes contact with the valve seat 139. When a relation of S1×(P1−P2)≤S3×(P3−P1) is satisfied, the movable portion 120 is separated from the valve seat 139.

Next, the configuration of the piezoelectric pump 10 will be described in detail with reference to FIG. 6, FIG. 7, and FIG. 8.

Figure 6:
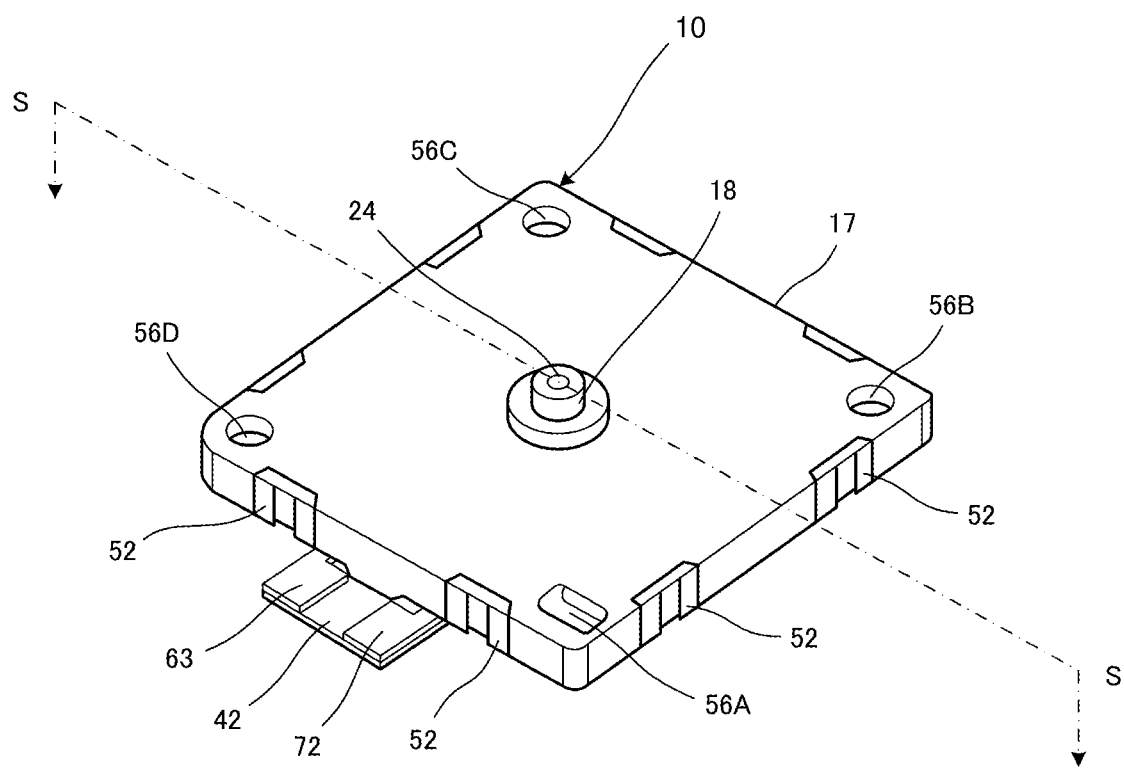
FIG. 6 is an outer appearance perspective view of a piezoelectric pump 10 illustrated in FIG. 1.
Figure 7:
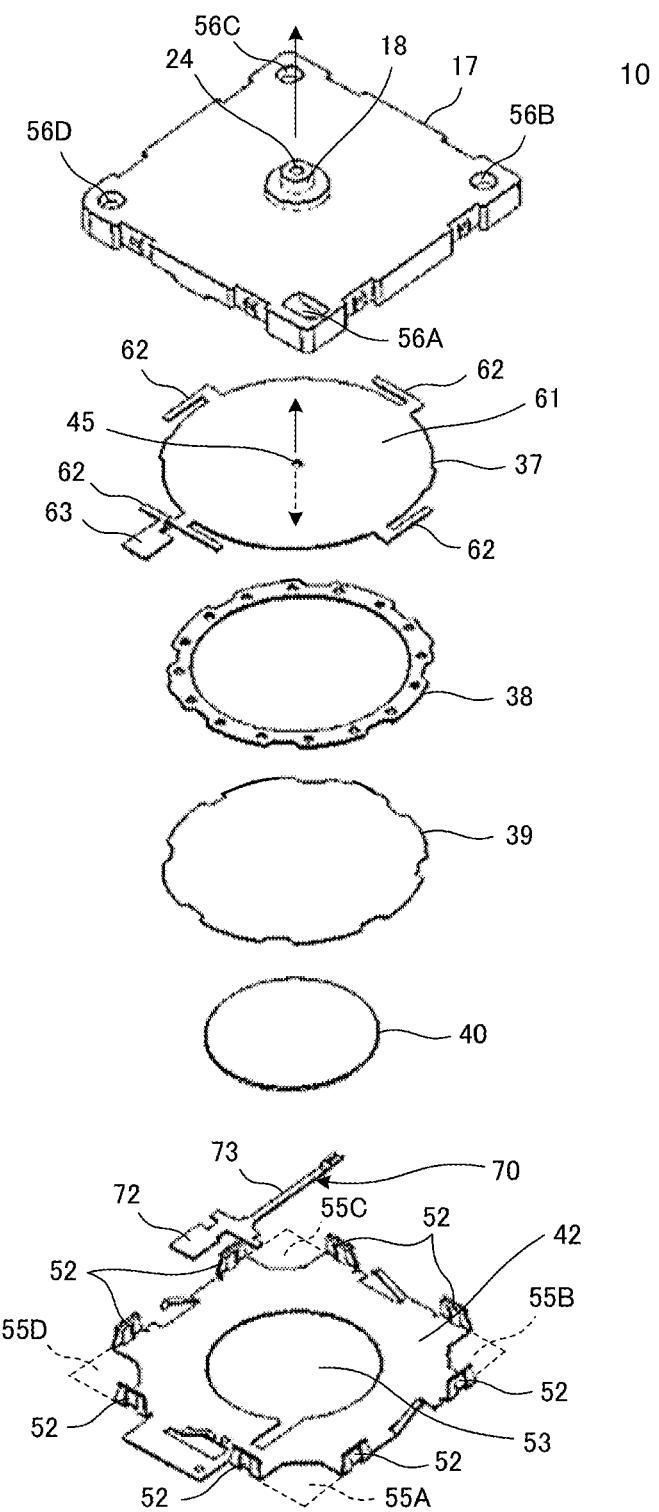
FIG. 7 is an exploded perspective view of the piezoelectric pump 10 illustrated in FIG. 6.

FIG. 6 is an outer appearance perspective view of the piezoelectric pump 10 illustrated in FIG. 1. FIG. 7 is an exploded perspective view of the piezoelectric pump 10 illustrated in FIG. 6. FIG. 8 is a cross-sectional view of the piezoelectric pump 10 illustrated in FIG. 6 cut along the line S-S.

The piezoelectric pump 10 includes an outer housing 17, a top plate 37, a side plate 38, a vibration plate 39, a piezoelectric element 40, and a cap 42 in this order from the upper side, and has the configuration in which they are laminated in order. The top plate 37, the side plate 38, and the vibration plate 39 configure a pump chamber 36. The piezoelectric pump 10 has dimensions of a width 20 mm, a length 20 mm, and a height 1.85 mm of a region other than a nozzle 18.

The outer housing 17 has the nozzle 18 in which the discharge hole 24 for discharging the air is formed at the center. The nozzle 18 has dimensions of a diameter 2.0 mm of an outer shape, a diameter 0.8 mm of an inner shape (that is, the discharge hole 24), and a height 1.6 mm. Screw holes 56A to 56D are formed in four corners of the outer housing 17.

The outer housing 17 is formed to have a U-shaped cross section the lower side of which is opened. The outer housing 17 accommodates therein the top plate 37 of the pump chamber 36, the side plate 38 of the pump chamber 36, the vibration plate 39, and the piezoelectric element 40. The outer housing 17 is made of, for example, resin.

The top plate 37 of the pump chamber 36 has a disc-like shape and is made of, for example, metal. In the top plate 37, a center portion 61, key-shaped projections 62 projecting from the center portion 61 in the horizontal direction and abutting against inner walls of the outer housing 17, and an external terminal 63 for connection to an external circuit are formed.

Furthermore, a ventilation hole 45 for communicating the inside and the outside of the pump chamber 36 is provided in the center portion 61 of the top plate 37. The ventilation hole 45 is formed at a position opposing the discharge hole 24 of the outer housing 17. The top plate 37 is bonded to the upper surface of the side plate 38.

The side plate 38 of the pump chamber 36 has an annular ring-shape, and is made of, for example, metal. The side plate 38 is bonded to the upper surface of the vibration plate 39. Therefore, the thickness of the side plate 38 corresponds to the height of the pump chamber 36.

The vibration plate 39 has a disc-like shape, and is made of, for example, metal. The vibration plate 39 configures the bottom surface of the pump chamber 36.

The piezoelectric element 40 has a disc-like shape, and is made of, for example, PZT-based ceramic. The piezoelectric element 40 is bonded to the main surface of the vibration plate 39 at the opposite side to the pump chamber 36 and is bent in accordance with an applied AC voltage. The piezoelectric element 40 and the vibration plate 39 configure an actuator.

A joint body of the top plate 37, the side plate 38, the vibration plate 39, and the piezoelectric element 40 is elastically supported on the outer housing 17 with the four projections 62 provided in the top plate 37.

An electrode conduction plate 70 is configured by an internal terminal 73 for connection to the piezoelectric element 40 and an external terminal 72 for connection to an external circuit. An end portion of the internal terminal 73 is soldered to a flat plate surface of the piezoelectric element 40. A soldering position is set to a position corresponding to a node of bending vibration of the piezoelectric element 40, thereby further suppressing vibration of the internal terminal 73.

The suction hole 53 having a disc-like shape is formed in the cap 42. The diameter of the suction hole 53 is larger than the diameter of the piezoelectric element 40. Furthermore, cutouts 55A to 55D are formed in the cap 42 at positions corresponding to the screw holes 56A to 56D of the outer housing 17.

The cap 42 has projections 52 projecting to the top plate 37 side on the outer circumferential edges thereof. The cap 42 holds the outer housing 17 with the projections 52, and accommodates the top plate 37 of the pump chamber 36, the side plate 38 of the pump chamber 36, the vibration plate 39, and the piezoelectric element 40 together with the outer housing 17. The cap 42 is made of, for example, resin.

Figure 8:
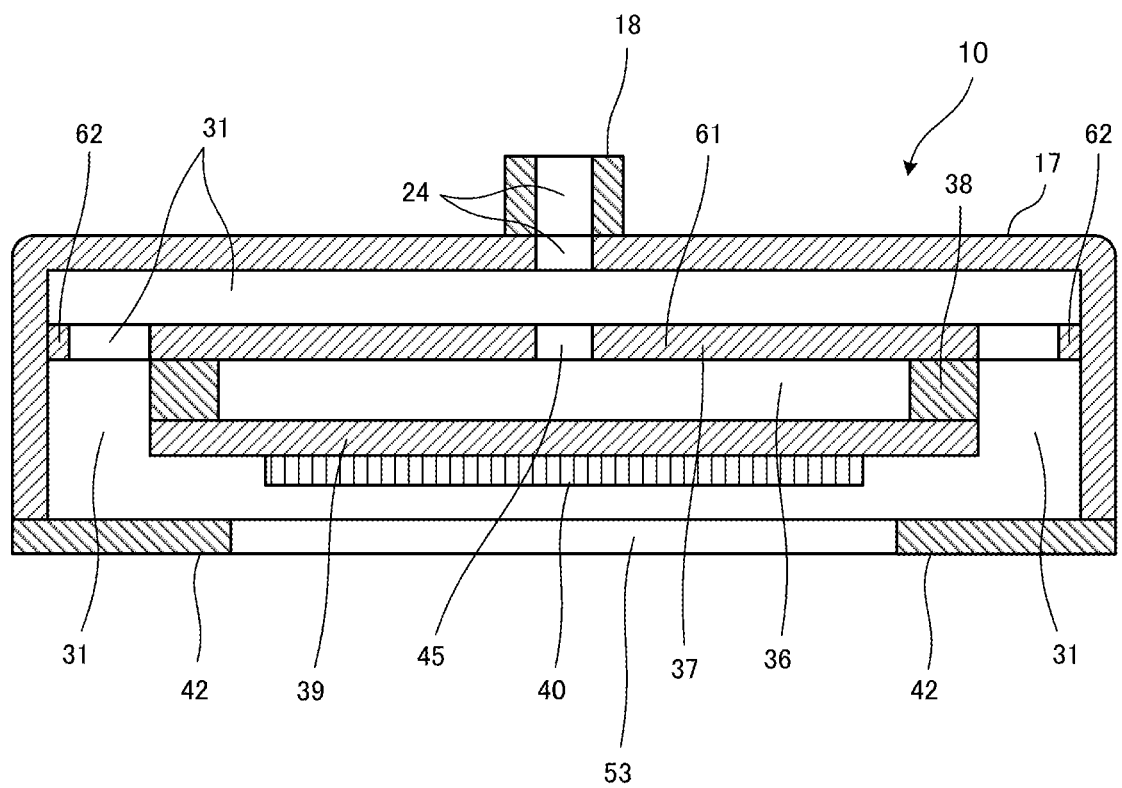
FIG. 8 is a cross-sectional view of the piezoelectric pump 10 illustrated in FIG. 6 cut along a line S-S.

As illustrated in FIG. 8, a ventilation path 31 is formed between the joint body of the top plate 37, the side plate 38, the vibration plate 39, and the piezoelectric element 40, and the outer housing 17 and the cap 42.

Next, operations of the piezoelectric pump 10 when being driven will be described.

FIGS. 9A and 9B are cross-sectional views of the piezoelectric pump 10 illustrated in FIG. 3 cut along the line S-S when the piezoelectric pump 10 is operated at a frequency (fundamental waves) in a primary mode. Arrows in the drawings indicate the air flow.

When an AC driving voltage at the frequency (fundamental waves) in the primary mode is applied to the piezoelectric element 40 from the external terminals 63 and 72 in a state illustrated in FIG. 8, the vibration plate 39 concentrically vibrates in a bending manner. At the same time, fluctuation in the pressure in the pump chamber 36 with the bending vibration of the vibration plate 39 causes the top plate 37 to concentrically vibrate in a bending manner with the bending vibration of the vibration plate 39 (with a vibration phase delay of 180° in the embodiment).

With this, as illustrated in FIGS. 9A and 9B, the vibration plate 39 and the top plate 37 are bent and deformed and the volume of the pump chamber 36 periodically changes.

As illustrated in FIG. 9A, when the AC voltage is applied to the piezoelectric element 40 to cause the vibration plate 39 to bend to the piezoelectric element 40 side, the volume of the pump chamber 36 is increased. With this increase, the air at the outside of the piezoelectric pump 10 is sucked into the pump chamber 36 while passing through the suction hole 53, the ventilation path 31, and the ventilation hole 45. No air flows out from the pump chamber 36 but inertial force of the air flow to the outside of the piezoelectric pump 10 from the discharge hole 24 acts.

As illustrated in FIG. 9B, when the AC voltage is applied to the piezoelectric element 40 to cause the vibration plate 39 to bend to the pump chamber 36 side, the volume of the pump chamber 36 is decreased. With this decrease, the air in the pump chamber 36 is discharged from the discharge hole 24 while passing through the ventilation hole 45 and the ventilation path 31.

At this time, the air that is discharged from the pump chamber 36 is discharged from the discharge hole 24 while drawing the air at the outside of the piezoelectric pump 10 through the suction hole 53 and the ventilation path 31. Therefore, in the piezoelectric pump 10, a flow rate of the air that is discharged from the discharge hole 24 is increased by a flow rate of the drawn air.

Next, air flow in the fluid control device 100 will be described.

Figure 10:
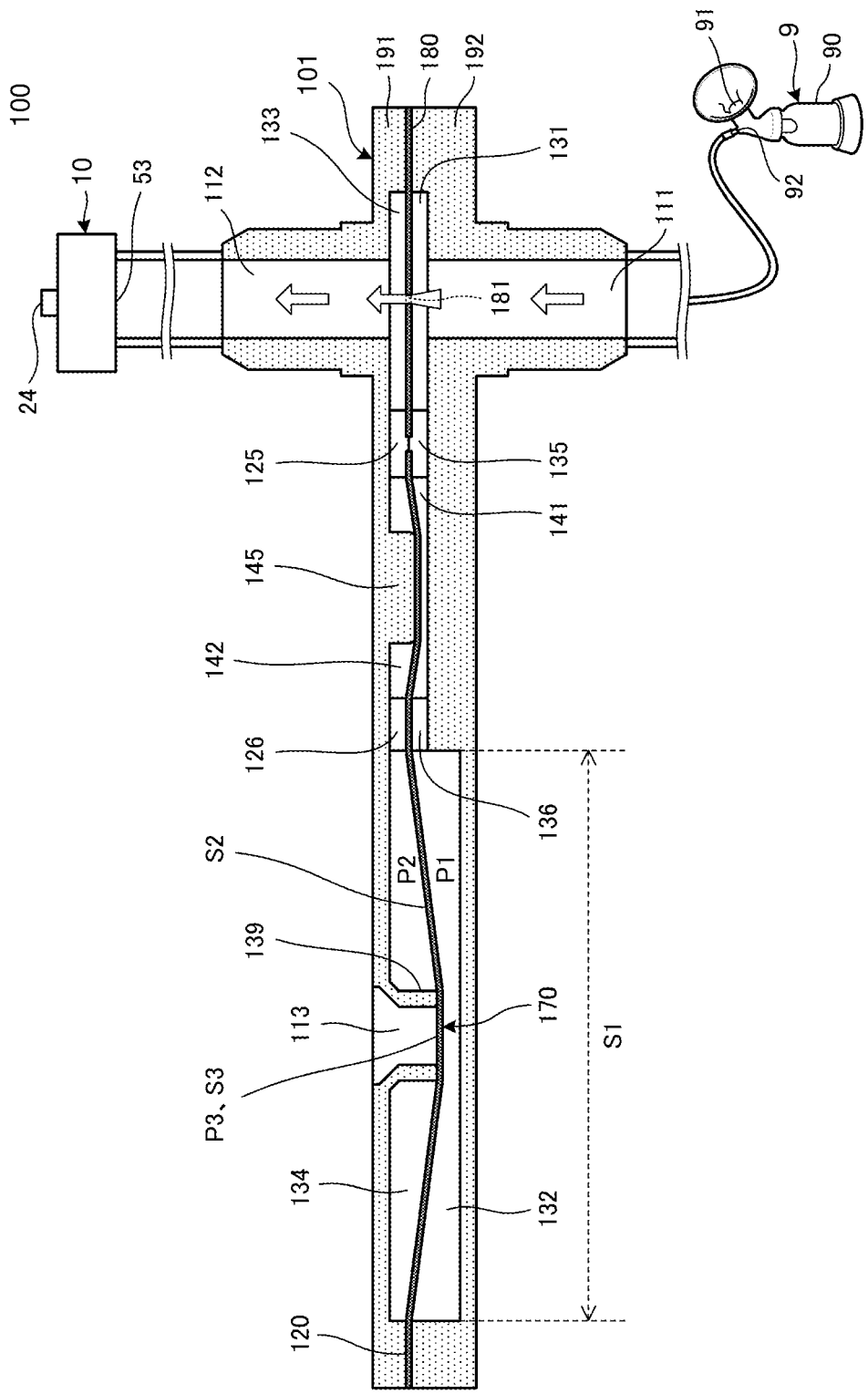
FIG. 10 is a descriptive view for explaining the air flow in the fluid control device 100 while the piezoelectric pump 10 is being driven.

FIG. 10 is a descriptive view for explaining the air flow in the fluid control device 100 while the piezoelectric pump 10 is being driven. Arrows in FIG. 10 indicate the air flow.

It should be noted that as described above, the first lower valve chamber 131, the communication path 135, the second lower valve chamber 141, the communication path 136, and the third lower valve chamber 132 correspond to the "first region" according to the disclosure. The first upper valve chamber 133, the communication path 125, the second upper valve chamber 142, the communication path 126, and the third upper valve chamber 134 correspond to the "second region" according to the disclosure. The valve seat 139 corresponds to the "valve seat" according to the disclosure.

First, a user attaches the inhalation port 91 of the inhaler 9 to, for example, the breast of the human being or the animal. The pressure in the container 90 before the piezoelectric pump 10 is driven is the atmospheric pressure. The fluid control device 100 turns the piezoelectric pump 10 ON when inhalation of liquid with the inhaler 9 is started.

When the piezoelectric pump 10 is driven, the air in the first upper valve chamber 133 is sucked into the piezoelectric pump 10 while passing through the second ventilation hole 112 and the suction hole 53. Then, the air in the piezoelectric pump 10 is discharged from the discharge hole 24.

In the fixed portion 180 of the valve body 190, although the first lower valve chamber 131 and the first upper valve chamber 133 communicate with each other with the first through-hole 181 interposed therebetween, pressure loss (flow path resistance) is generated with the first through-hole 181. For this reason, the pressure in the first lower valve chamber 131 is higher than the pressure in the first upper valve chamber 133.

Furthermore, in the exhaust valve 170, the pressure in the third lower valve chamber 132 is higher than the pressure in the third upper valve chamber 134. Therefore, the movable portion 120 closes the third ventilation hole 113 using a pressure difference between the third lower valve chamber 132 and the third upper valve chamber 134. The movable portion 120 thereby blocks communication between the second ventilation hole 112 and the third ventilation hole 113.

That is to say, when the pressure in the first region is higher than the pressure in the second region, the valve body 190 blocks communication between the second ventilation hole 112 and the third ventilation hole 113 and communicates the first ventilation hole 111 and the second ventilation hole 112 with each other with the first through-hole 181 interposed therebetween.

Therefore, the air flows to the second ventilation hole 112 from the first ventilation hole 111 while passing through the first through-hole 181. The air flowed out from the second ventilation hole 112 is sucked into the piezoelectric pump 10 while passing through the suction hole 53 to be discharged from the discharge hole 24.

As a result, the air in the container 90 of the inhaler 9 is discharged to the second lower valve chamber 141 of the valve 101 from the connection hole 92 while passing through the first ventilation hole 111. With this, the pressure (air pressure) in the container 90 becomes lower than the atmospheric pressure and is made to be a negative pressure.

Therefore, the inhaler 9 can inhale the liquid (for example, breast milk, or the like) at the outside of the container 90 into the container 90 from the inhalation port 91. The inhaler 9 stores the liquid in the container 90 and discharges the air in the container 90 from the connection hole 92.

Figure 11:
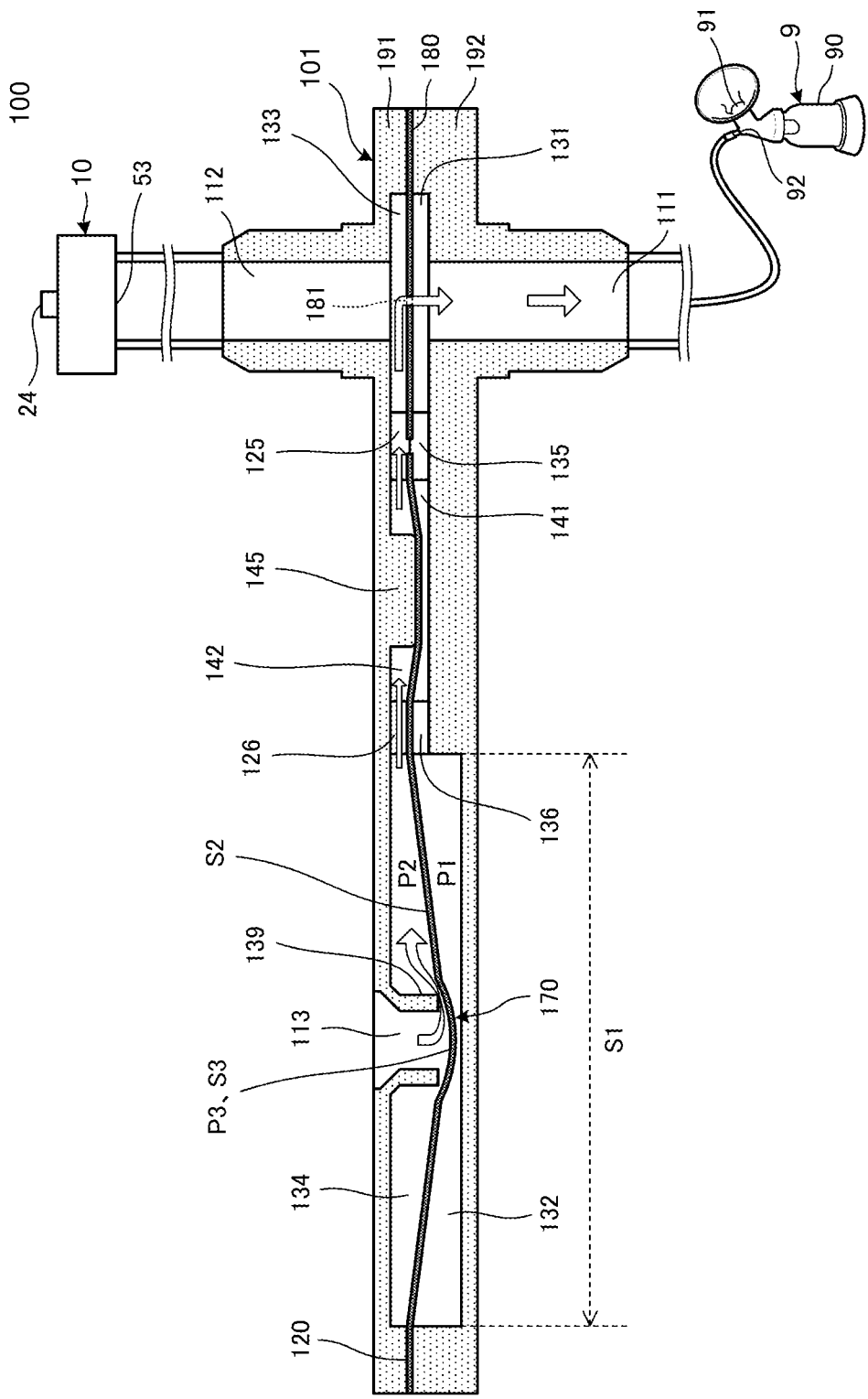
FIG. 11 is a descriptive view for explaining the air flow in the fluid control device 100 when driving of the piezoelectric pump 10 is stopped, a pressure in a container 90 reaches a maximum suction pressure of the piezoelectric pump 10, or a flow path is closed.

FIG. 11 is a descriptive view for explaining air flow in the fluid control device 100 when driving of the piezoelectric pump 10 is stopped, the pressure in the container 90 reaches a maximum suction pressure of the piezoelectric pump 10, or a flow path is closed. Arrows in FIG. 11 indicate air flow.

When driving of the piezoelectric pump 10 is stopped, the pressure in the container 90 reaches the maximum suction pressure of the piezoelectric pump 10, or the flow path such as the tube is closed, the pressure in the first lower valve chamber 131 becomes equal to the pressure in the first upper valve chamber 133 with the first through-hole 181.

It should be noted that the pressure in the first lower valve chamber 131 and the pressure in the first upper valve chamber 133 are equal to or lower than the atmospheric pressure. Therefore, in the exhaust valve 170, the movable portion 120 is separated from the valve seat 139 to open the third ventilation hole 113.

That is to say, when the pressure in the first region is equal to or lower than the pressure in the second region, the valve body 190 communicates the second ventilation hole 112 and the third ventilation hole 113 with each other and communicates the first ventilation hole 111 and the second ventilation hole 112 with each other with the first through-hole 181 interposed therebetween.

Therefore, the air flows in from the third ventilation hole 113, and flows to the first ventilation hole 111 while passing through the third upper valve chamber 134, the communication path 126, the second upper valve chamber 142, the first upper valve chamber 133, the first through-hole 181, and the first lower valve chamber 131, as illustrated in FIG. 11. Thereafter, the air flowed out from the first ventilation hole 111 flows into the container 90 while passing through the tube.

The pressure (air pressure) in the container 90 is thereby increased to be returned to the atmospheric pressure. This enables the inhalation port 91 of the inhaler 9 to be easily detached from the breast of the human being or the animal.

As described above, the valve 101 in the embodiment opens and closes the third ventilation hole 113 with the pressure difference between the first region and the second region by the flow path resistance of the first through-hole 181.

Accordingly, the valve 101 in the embodiment can perform the fluid suction operation and can passively release the pressure in the flow path to the atmosphere without providing special components such as a pressure sensor, a flowmeter, and an electromagnetic valve.

Unlike the electromagnetic valve, the valve 101 passively opens and closes the valve as described above. This enables the valve 101 to reduce power consumption in comparison with the electromagnetic valve. The valve 101 is therefore preferable for a breast pump that is required to be driven with less power consumption.

Furthermore, the fluid control device 100 including the valve 101 in the embodiment also provides the same effects.

Next, three valves 101 obtained by changing the diameter D1 of the first through-hole 181 are compared.

Figure 12:
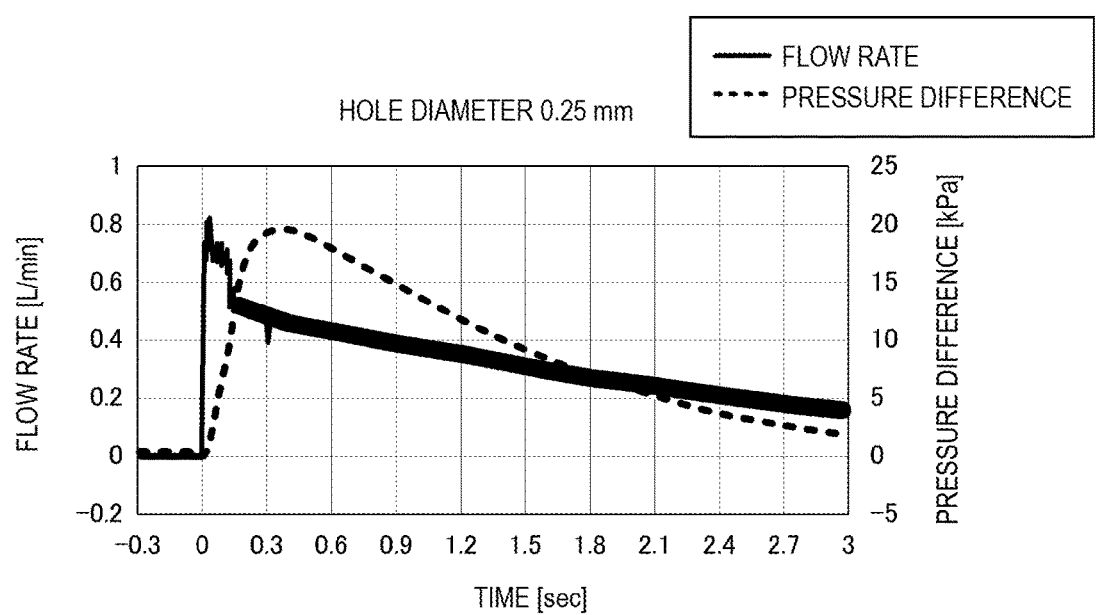
FIG. 12 is a graph illustrating a result of the measurement of a pressure difference between a first ventilation hole 111 and a second ventilation hole 112 of the valve 101 in which a diameter D1 of a first through-hole 181 is 0.25 mm and a flow rate of the air flowing out from the second ventilation hole 112 while the piezoelectric pump 10 is being driven.
Figure 13:
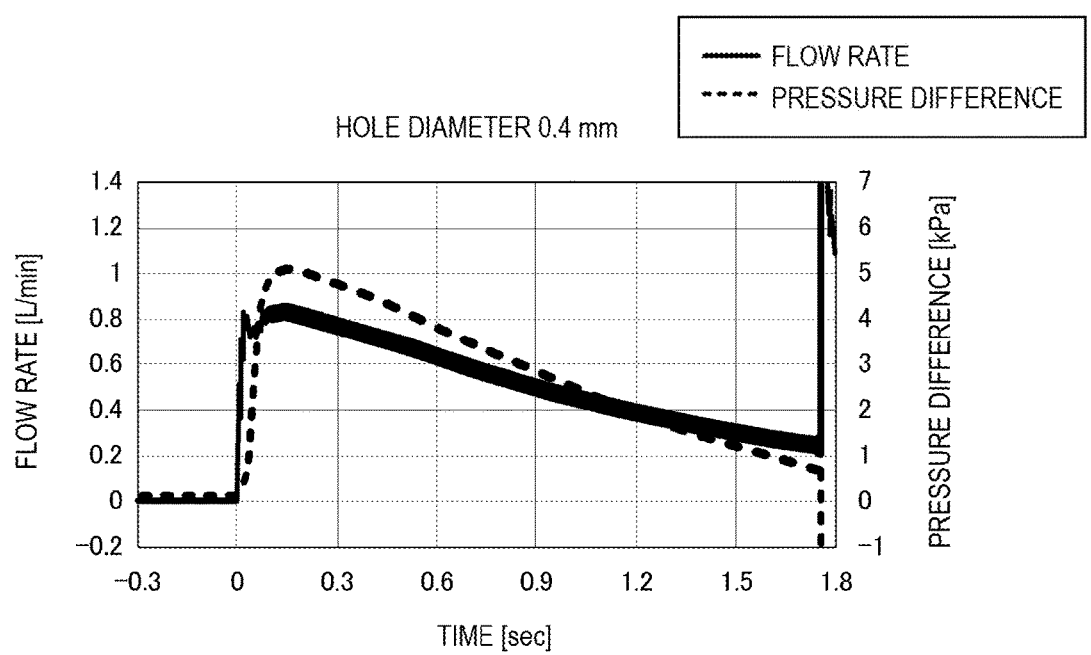
FIG. 13 is a graph illustrating a result of the measurement of the pressure difference between the first ventilation hole 111 and the second ventilation hole 112 of the valve 101 in which the diameter D1 of the first through-hole 181 is 0.40 mm and the flow rate of the air flowing out from the second ventilation hole 112 while the piezoelectric pump 10 is being driven.
Figure 14:
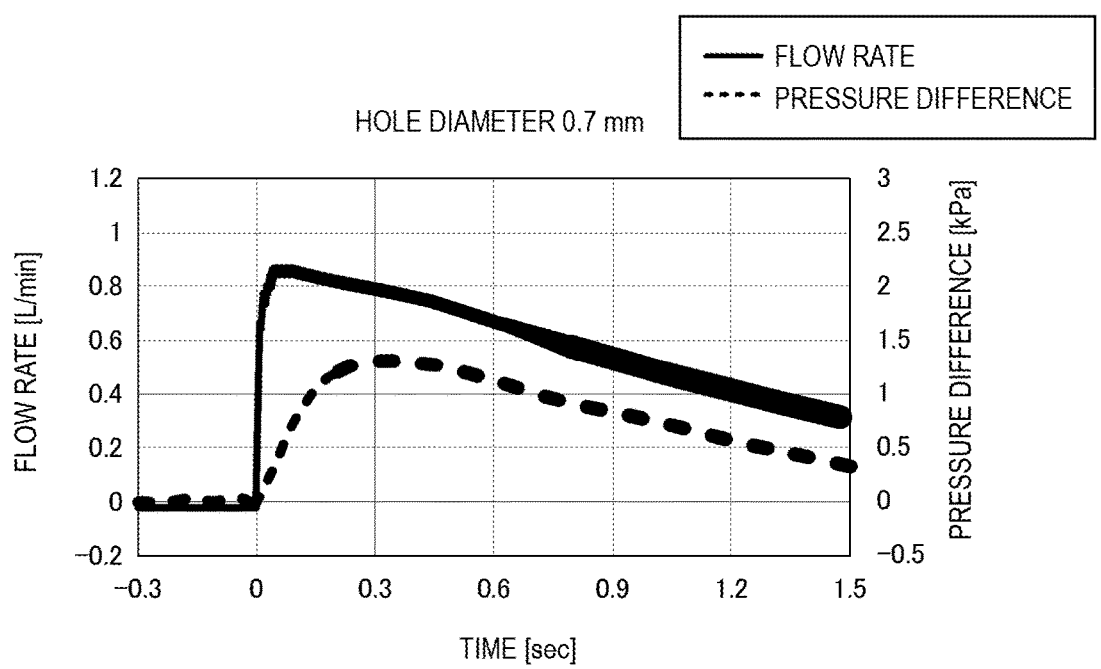
FIG. 14 is a graph illustrating a result of the measurement of the pressure difference between the first ventilation hole 111 and the second ventilation hole 112 of the valve 101 in which the diameter D1 of the first through-hole 181 is 0.70 mm and the flow rate of the air flowing out from the second ventilation hole 112 while the piezoelectric pump 10 is being driven.

FIG. 12 is a graph illustrating a result of measurement of the pressure difference between the first ventilation hole 111 and the second ventilation hole 112 of the valve 101 in which the diameter D1 of the first through-hole 181 is 0.25 mm and a flow rate of the air flowing out from the second ventilation hole 112 while the piezoelectric pump 10 is being driven. FIG. 13 is a graph illustrating a result of measurement of the pressure difference between the first ventilation hole 111 and the second ventilation hole 112 of the valve 101 in which the diameter D1 of the first through-hole 181 is 0.40 mm and the flow rate of the air flowing out from the second ventilation hole 112 while the piezoelectric pump 10 is being driven. FIG. 14 is a graph illustrating a result of measurement of the pressure difference between the first ventilation hole 111 and the second ventilation hole 112 of the valve 101 in which the diameter D1 of the first through-hole 181 is 0.70 mm and the flow rate of the air flowing out from the second ventilation hole 112 while the piezoelectric pump 10 is being driven.

First, the three valves 101 having the diameters D1 of the first through-holes 181, which are 0.25 mm, 0.40 mm, and 0.70 mm, are prepared. Then, with conditions under which the piezoelectric pumps 10 are connected to the second ventilation holes 112 of the respective valves 101 and the piezoelectric pumps 10 are driven, Table 1 to Table 3 indicate results of the measurement of the pressure differences (kPa) between the first ventilation holes 111 and the second ventilation holes 112 of the respective valves 101 and the flow rates (L/min) of the air flowing out from the second ventilation holes 112.

TABLE 1

| FLOW RATE L/min | PRESSURE DIFFERENCE (THEORETICAL VALUE) kPa | PRESSURE DIFFERENCE (EXPERIMENTAL VALUE) kPa |
| --- | --- | --- |
| 0.2 | 2.9 | 3.5 |
| 0.3 | 6.7 | 9.0 |
| 0.4 | 11.9 | 14.5 |
| 0.5 | 18.6 | 19.5 |

TABLE 2

| FLOW RATE L/min | PRESSURE DIFFERENCE (THEORETICAL VALUE) kPa | PRESSURE DIFFERENCE (EXPERIMENTAL VALUE) kPa |
| --- | --- | --- |
| 0.35 | 1.4 | 1.6 |
| 0.5 | 2.8 | 2.8 |
| 0.65 | 4.8 | 4.0 |
| 0.8 | 7.3 | 5.2 |

TABLE 3

| FLOW RATE L/min | PRESSURE DIFFERENCE (THEORETICAL VALUE) kPa | PRESSURE DIFFERENCE (EXPERIMENTAL VALUE) kPa |
| --- | --- | --- |
| 0.35 | 0.1 | 0.4 |
| 0.5 | 0.3 | 0.7 |
| 0.65 | 0.5 | 1.0 |
| 0.8 | 0.8 | 1.3 |

It should be noted that in Table 1 to Table 3, the pressure difference (experimental value) indicates a value obtained by practically measuring the pressure in the first ventilation hole 111 and the pressure in the second ventilation hole 112 and calculating the difference between both of the pressures. By contrast, the pressure difference (theoretical value) indicates a value obtained by calculating the difference between both the pressures by a simulator.

The pressure difference (experimental value) and the flow rate in Table 1 correspond to the graph in FIG. 12. In the same manner, the pressure difference (experimental value) and the flow rate in Table 2 correspond to the graph in FIG. 13. The pressure difference (experimental value) and the flow rate in Table 3 correspond to the graph in FIG. 14.

This experiment shows that in the valve 101, as the diameter D1 of the first through-hole 181 becomes larger, the flow rate is increased and the pressure difference is decreased.

The above-mentioned result is considered to be obtained because as the diameter D1 of the first through-hole 181 becomes larger, the flow path resistance of the first through-hole 181 is decreased.

The Bernoulli's theorem "$p1/\rho + v1^2/2 = p2/\rho + v2^2/2$" is satisfied when the cross-sectional area of the first through-hole 181 is s1, the flow velocity of the air passing through the first through-hole 181 is v1, the flow rate of the air passing through the first through-hole 181 is q1, the pressure of the air passing through the first through-hole 181 is p1, the cross-sectional area of the first upper valve chamber 133 is s2, the flow velocity of the air passing through the first upper valve chamber 133 is v2, the flow rate of the air passing through the first upper valve chamber 133 is q2, the pressure of the air passing through the first upper valve chamber 133 is p2, and the air density is $\rho$. The following pressure difference "$p1 - p2 = \rho \cdot v1^2/2 = \rho \cdot (q1/s1)^2/2$" can be derived from the Bernoulli's theorem.

It should be noted that $v2 \cong 0$ may be considered to be satisfied at a place having a sufficiently larger cross-sectional area than s1.

Furthermore, the Bernoulli's theorem requires the diameter D1 of the first through-hole 181 to be sufficiently smaller than diameters D2 of the first upper valve chamber 133 and the first lower valve chamber 131. Therefore, an error can be calculated to be equal to or lower than 10% when the diameter D1 of the first through-hole 181 is equal to or smaller than 1/3 of the diameters D2 of the first upper valve chamber 133 and the first lower valve chamber 131.

In addition, the length L of the first through-hole 181 needs to be in a range in which air resistance (loss) when the air flows through the first through-hole 181 can be considered to be sufficiently low. The length L of the first through-hole 181 is equal to the thickness of the fixed portion 180. Loss when the air flows through the first through-hole 181 can be roughly estimated from the Poiseuille's equation. An error can be calculated to be equal to or lower than 10% when the length L of the first through-hole 181 is equal to or smaller than the length of twice the diameter D1 of the first through-hole 181.

Accordingly, for example, in the case in which the diameter D2 illustrated in FIG. 1 is 10 mm, when the diameter D1 is 0.25 mm to 0.7 mm, the above-described relation of D1<D2/3 is satisfied. Furthermore, when the length L of the first through-hole 181 is 0.1 mm, the above-described relation of L<2D1 is satisfied.

Hereinafter, a fluid control device 200 according to a second embodiment of the disclosure will be described.

Figure 15:
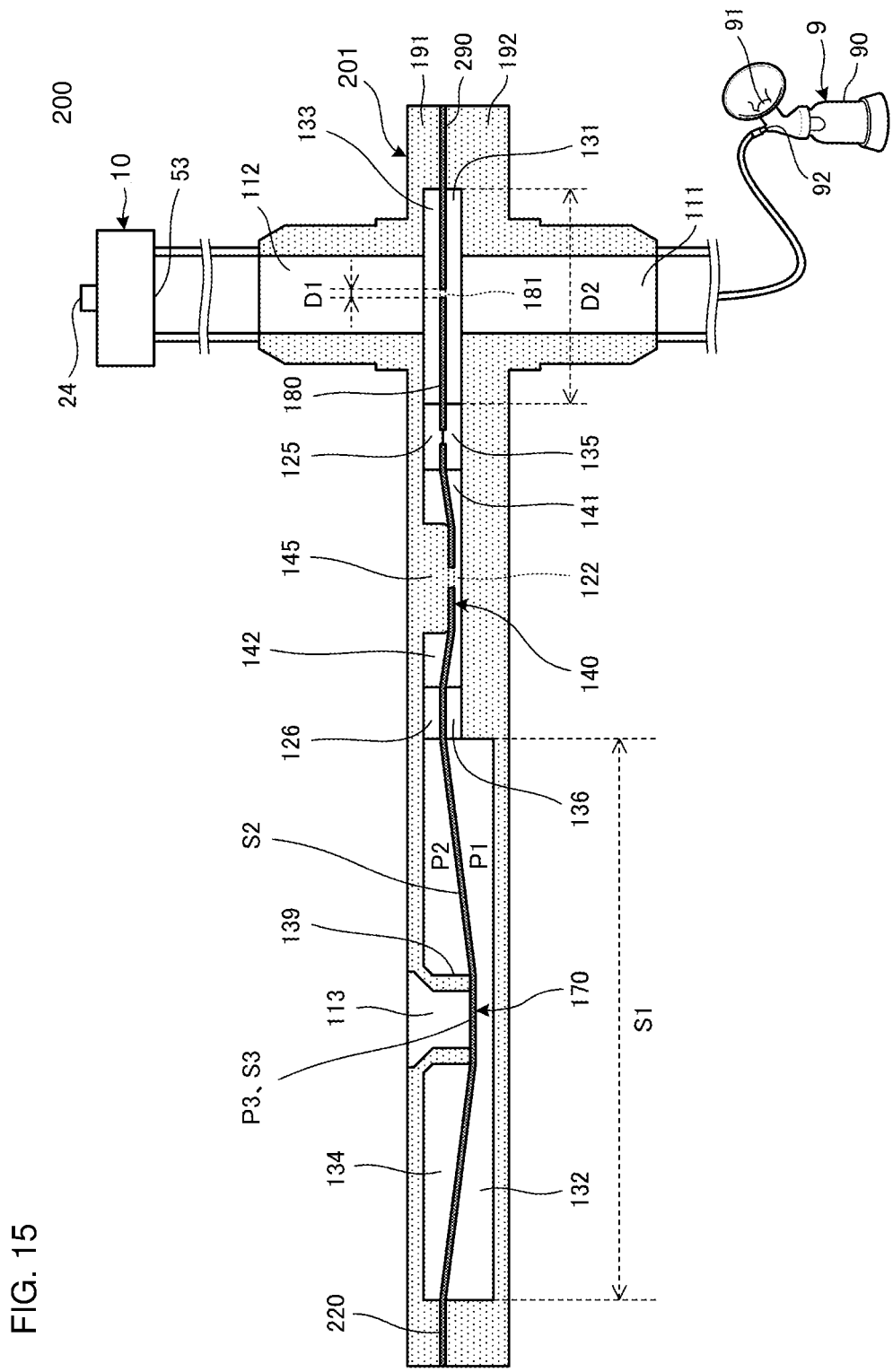
FIG. 15 is a cross-sectional view of a fluid control device 200 according to a second embodiment of the disclosure.

FIG. 15 is a cross-sectional view of the fluid control device 200 according to the second embodiment of the disclosure. The fluid control device 200 is different from the fluid control device 100 in a point that a valve 201 has a second through-hole 122. The circular second through-hole 122 is provided in a movable portion 220 of a valve body 290 at a center portion of a region opposing the valve seat 145. Other configurations thereof are the same and description thereof is therefore omitted.

The diameter of the second through-hole 122 is smaller than the diameter of the surface of the valve seat 145 abutting against the movable portion 220.

As illustrated in FIG. 15, the valve body 290 is fixed to the first valve housing 191 and the second valve housing 192 such that a part of the movable portion 220 makes contact with the valve seat 139 and the circumference of the second through-hole 122 in the movable portion 220 makes contact with the valve seat 145. In this case, the valve seat 145 pressurizes the circumference of the second through-hole 122 in the valve body 290.

As illustrated in FIG. 15, the valve body 290 configures a check valve 140 together with the first valve housing 191 and the second valve housing 192. The check valve 140 is configured by the second lower valve chamber 141, the second upper valve chamber 142, the valve seat 145, and a region of the valve body 290, which faces the second lower valve chamber 141 and the second upper valve chamber 142.

In the check valve 140, the circumference of the second through-hole 122 in the valve body 290 abuts against or is separated from the valve seat 145 with a pressure difference between the second lower valve chamber 141 and the second upper valve chamber 142. With this, the check valve 140 allows air flow to the second lower valve chamber 141 from the second upper valve chamber 142 and blocks air flow to the second upper valve chamber 142 from the second lower valve chamber 141.

Next, air flow in the fluid control device 200 will be described.

Figure 16:
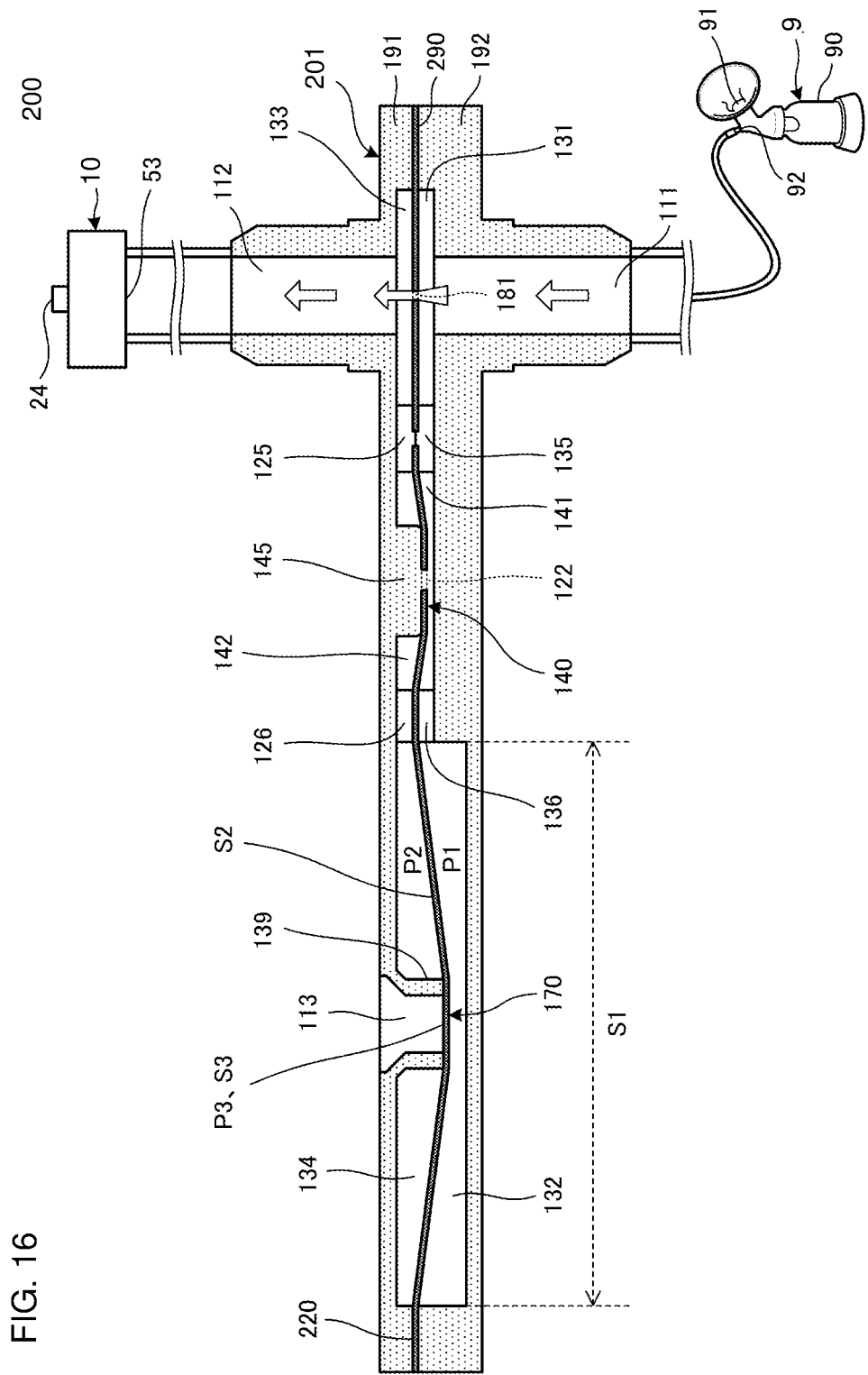
FIG. 16 is a descriptive view for explaining the air flow in the fluid control device 200 while the piezoelectric pump 10 is being driven.

FIG. 16 is a descriptive view for explaining air flow in the fluid control device 200 while the piezoelectric pump 10 is being driven.

The air flow in the fluid control device 200 while the piezoelectric pump 10 is being driven is the same as the air flow in the fluid control device 100 illustrated in FIG. 10. In the check valve 140, the pressure in the second lower valve chamber 141 is higher than the pressure in the second upper valve chamber 142. Therefore, a state in which the circumference of the second through-hole 122 in the movable portion 220 makes contact with the valve seat 145 is maintained.

Figure 17:
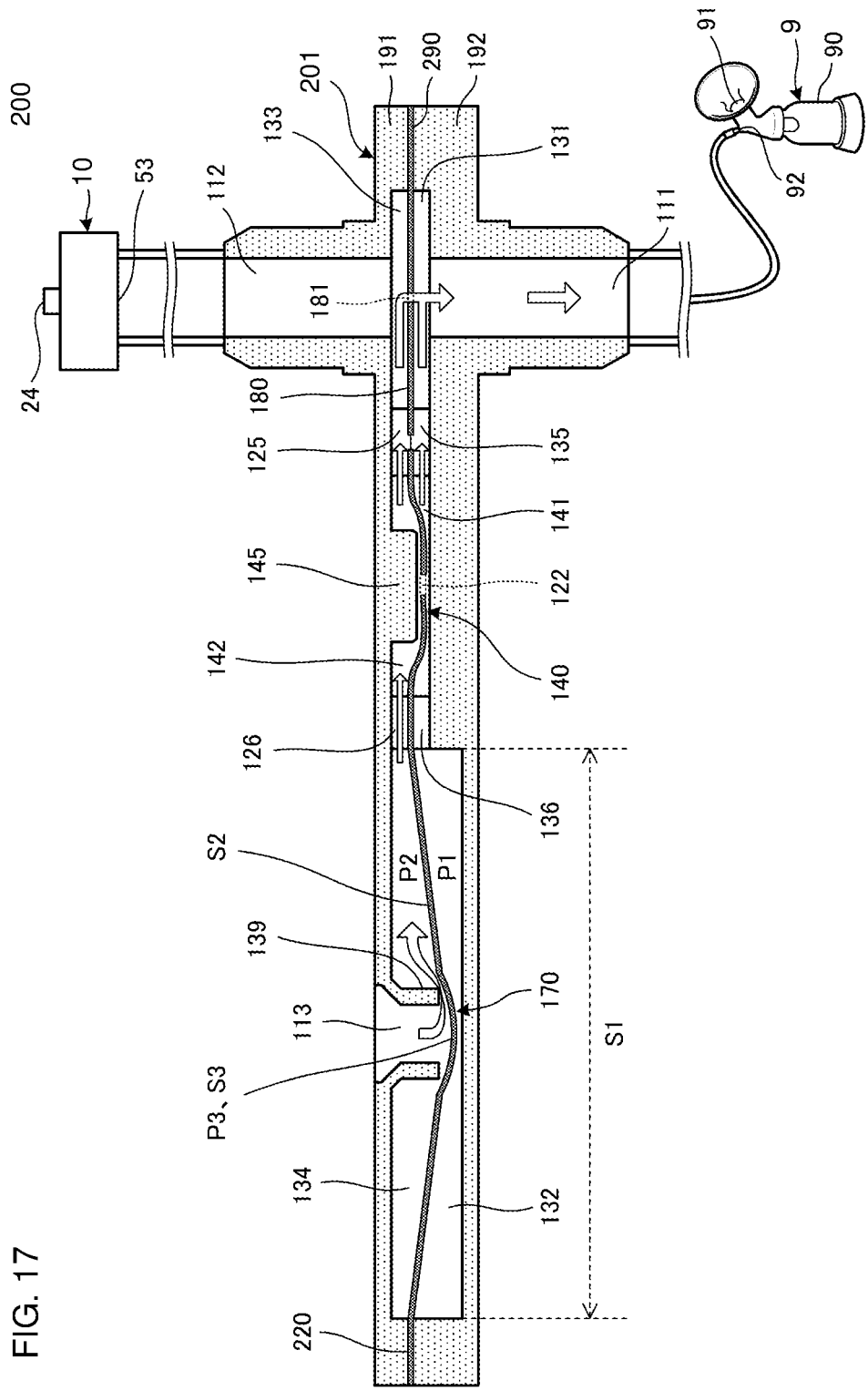
FIG. 17 is a descriptive view for explaining the air flow in the fluid control device 200 when driving of the piezoelectric pump 10 is stopped, the pressure in the container 90 reaches the maximum suction pressure of the piezoelectric pump 10, or the flow path is closed.

FIG. 17 is a descriptive view for explaining air flow in the fluid control device 200 when driving of the piezoelectric pump 10 is stopped, the pressure in the container 90 reaches the maximum suction pressure of the piezoelectric pump 10, or the flow path is closed.

When driving of the piezoelectric pump 10 is stopped, the pressure in the container 90 reaches the maximum suction pressure of the piezoelectric pump 10, or the flow path such as the tube is closed, the pressure in the first lower valve chamber 131 becomes equal to the pressure in the first upper valve chamber 133 with the first through-hole 181.

It should be noted that the pressure in the first lower valve chamber 131 and the pressure in the first upper valve chamber 133 are equal to or lower than the atmospheric pressure. Therefore, in the exhaust valve 170, the movable portion 220 is separated from the valve seat 139 to open the third ventilation hole 113.

That is to say, when the pressure in the first region is equal to or lower than the pressure in the second region, the valve body 290 communicates the second ventilation hole 112 and the third ventilation hole 113 with each other and communicates the first ventilation hole 111 and the second ventilation hole 112 with each other with the first through-hole 181 interposed therebetween.

Therefore, the air flows in from the third ventilation hole 113, and flows to the first ventilation hole 111 while passing through the third upper valve chamber 134, the communication path 126, the second upper valve chamber 142, the communication path 125, the first upper valve chamber 133, the first through-hole 181, and the first lower valve chamber 131 (see FIG. 17).

Furthermore, in the check valve 140, the pressure in the second lower valve chamber 141 becomes lower than the pressure in the second upper valve chamber 142 after the exhaust valve 170 is opened. Therefore, the circumference of the second through-hole 122 in the movable portion 220 is separated from the valve seat 145 to communicate the first ventilation hole 111 and the second region with each other. Therefore, the air flows to the first ventilation hole 111 from the third ventilation hole 113 while passing through the second through-hole 122.

That is to say, in the valve 201, the air flows to the first ventilation hole 111 from the third ventilation hole 113 while passing through both of the first through-hole 181 and the second through-hole 122.

With the air flow, in the valve 201, the air rapidly flows into the container 90 from the first ventilation hole 111. In the valve 201, the pressure (air pressure) in the container 90 is thereby increased to be returned to the atmospheric pressure rapidly.

Accordingly, the valve 201 can perform the fluid suction operation and can passively release the pressure in the flow path to the atmosphere for a short period of time. Unlike an electromagnetic valve, the valve 201 passively opens and closes the valve as described above. This enables the valve 201 to reduce power consumption in comparison with the electromagnetic valve. The valve 201 is therefore preferable for a breast pump that is required to be driven with less power consumption. Furthermore, the fluid control device 200 including the valve 201 in the embodiment also provides the same effects.

Hereinafter, a fluid control device 300 according to a third embodiment of the disclosure will be described.

Figure 18:
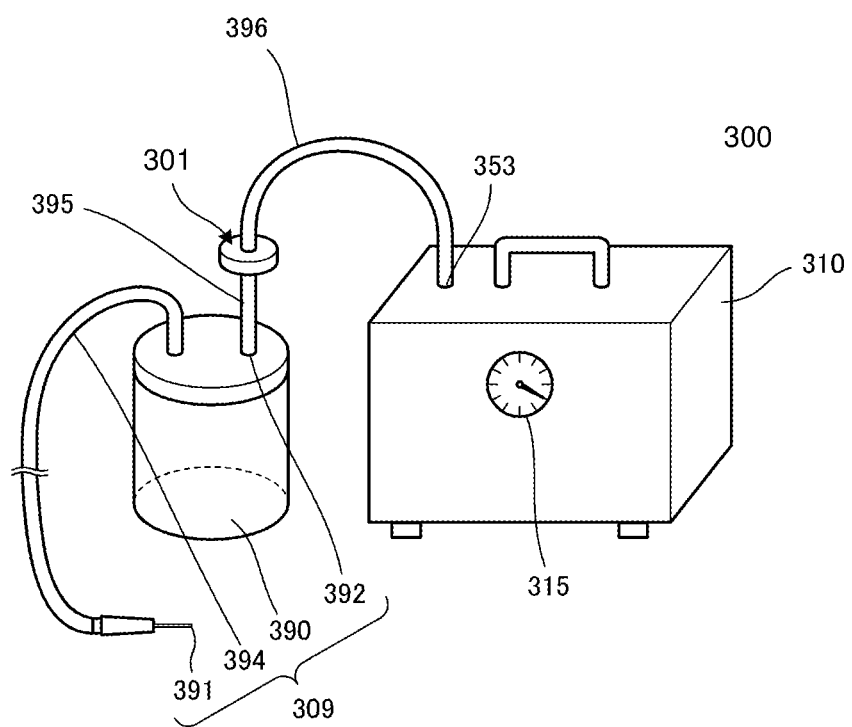
FIG. 18 is an outer appearance view of a fluid control device 300 according to a third embodiment of the disclosure.
Figure 19:
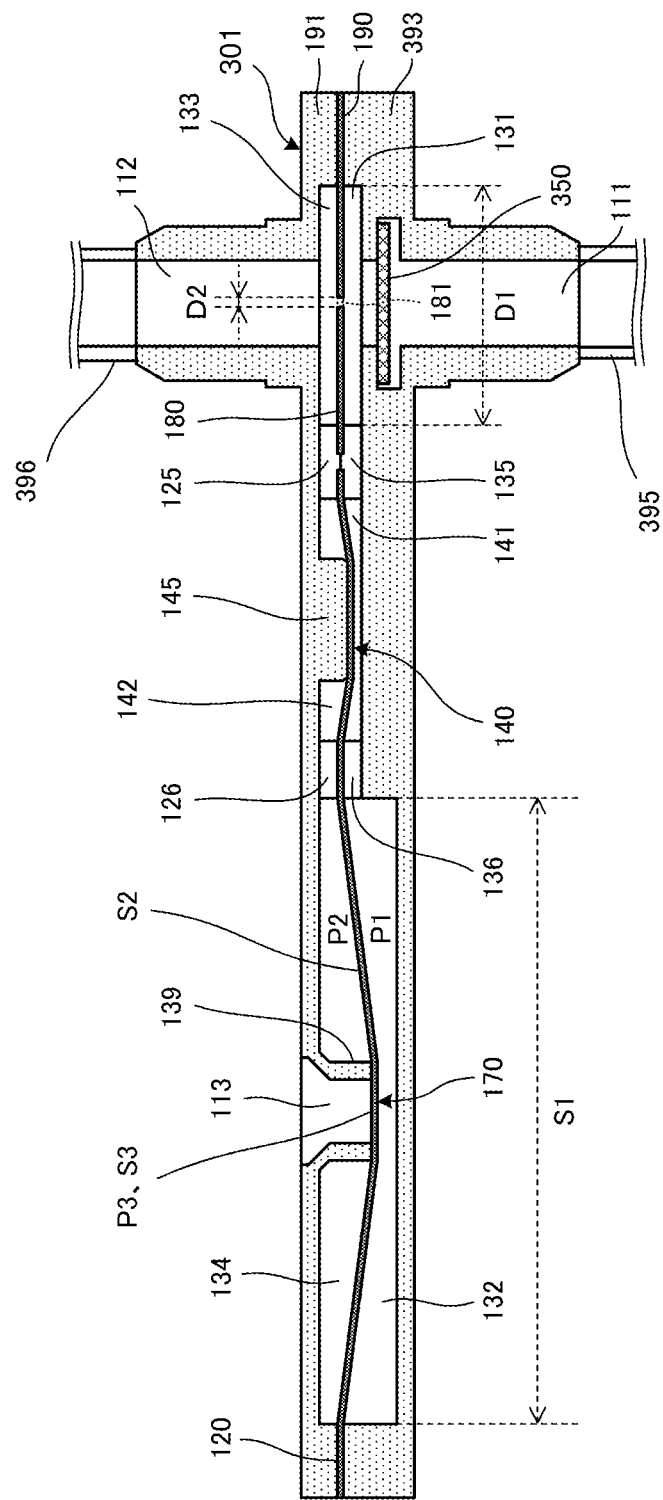
FIG. 19 is a cross-sectional view of a valve 301 illustrated in FIG. 18.

FIG. 18 is an outer appearance view of the fluid control device 300 according to the third embodiment of the disclosure. FIG. 19 is a cross-sectional view of a valve 301 illustrated in FIG. 18. The fluid control device 300 is a device that sucks liquid (for example, phlegm or the like). The fluid control device 300 includes a pump 310, an inhaler 309, and a valve 301.

The pump 310 has a suction hole 353 for sucking the air, a discharge hole (not illustrated) for discharging the air, and a pressure gauge 315 indicating a suction pressure of the air.

The inhaler 309 has a container 390, a connection hole 392, and a tube 394. An inhalation port 391 at the end portion of the tube 394 is inserted into, for example, an oral cavity of a human being or an animal. The container 390 stores therein the liquid (for example, phlegm or the like).

The valve 301 is different from the valve 101 in a point that a filter 350 is provided in a housing 393. The filter 350 passes gas and prevents passing of liquid. The filter 350 adsorbs, for example, bacterium in order to prevent infection and contamination. The filter 350 is bonded to an inner wall of the housing 393 with an adhesive or the like. Other configurations of the valve 301 are the same as those of the valve 101 and description thereof is therefore omitted.

In the above-described configuration, the inhalation port 391 is connected to the container 390 with the tube 394 interposed therebetween. The first ventilation hole 111 of the valve 301 is connected to the connection hole 392 of the inhaler 309 with a tube 395 interposed therebetween. The second ventilation hole 112 of the valve 301 is connected to the suction hole 353 of the pump 310 with a tube 396 interposed therebetween. The third ventilation hole 113 of the valve 301 is opened to the atmosphere.

Then, air flow in the fluid control device 300 while the pump 310 is being driven is substantially the same as the air flow in the fluid control device 100 illustrated in FIG. 10. The air flows in the fluid control device 300 while passing through the filter 350.

Air flow in the fluid control device 300 when driving of the pump 310 is stopped, the pressure in the container 390 reaches a maximum suction pressure of the pump 310, or a flow path is closed is also substantially the same as the air flow in the fluid control device 100 illustrated in FIG. 11. The air flows in the fluid control device 300 while passing through the filter 350.

For example, the inhalation port 391 is closed when sucking a tissue of a human body in a state in which there is no adsorption target. The closure of the inhalation port 391 lowers a flow rate and the pressure difference between the first region and the second region is 0. With this, the movable portion 120 automatically opens the third ventilation hole 113 to open the inhalation port 391 to the atmosphere.

Accordingly, the valve 301 provides the same effects as those provided by the valve 101. That is to say, the valve 301 can perform the fluid suction operation and can passively release the pressure in the flow path to the atmosphere. Furthermore, the fluid control device 300 including the valve 301 also provides the same effects.

When the liquid adheres to the filter 350 while the pump 310 is being driven, the filter 350 is clogged to increase flow path resistance (ventilation resistance) of the filter 350. That is to say, the fluid control device 300 cannot appropriately suck the air.

Although an existing common suction device also includes a filter, clogging of the filter cannot be detected. In the existing suction device, a nurse or other staff checks outer appearance of the filter, manages usage time of the filter, and so on to exchange the filter. That is to say, with the existing suction device, it is difficult to manage the filter in a quantitative manner.

On the other hand, with the valve 301 of the fluid control device 300, when the flow path resistance of the filter 350 is increased, the pressure difference between the first region and the second region is eliminated and the movable portion 120 opens the third ventilation hole 113. The atmosphere release generates sound when the air passes therethrough.

Accordingly, the valve 301 and the fluid control device 300 enable the nurse or the like to easily detect clogging of the filter 350 with the sound in the atmosphere release.

Hereinafter, a fluid control device 400 according to a fourth embodiment of the disclosure will be described.

Figure 20:
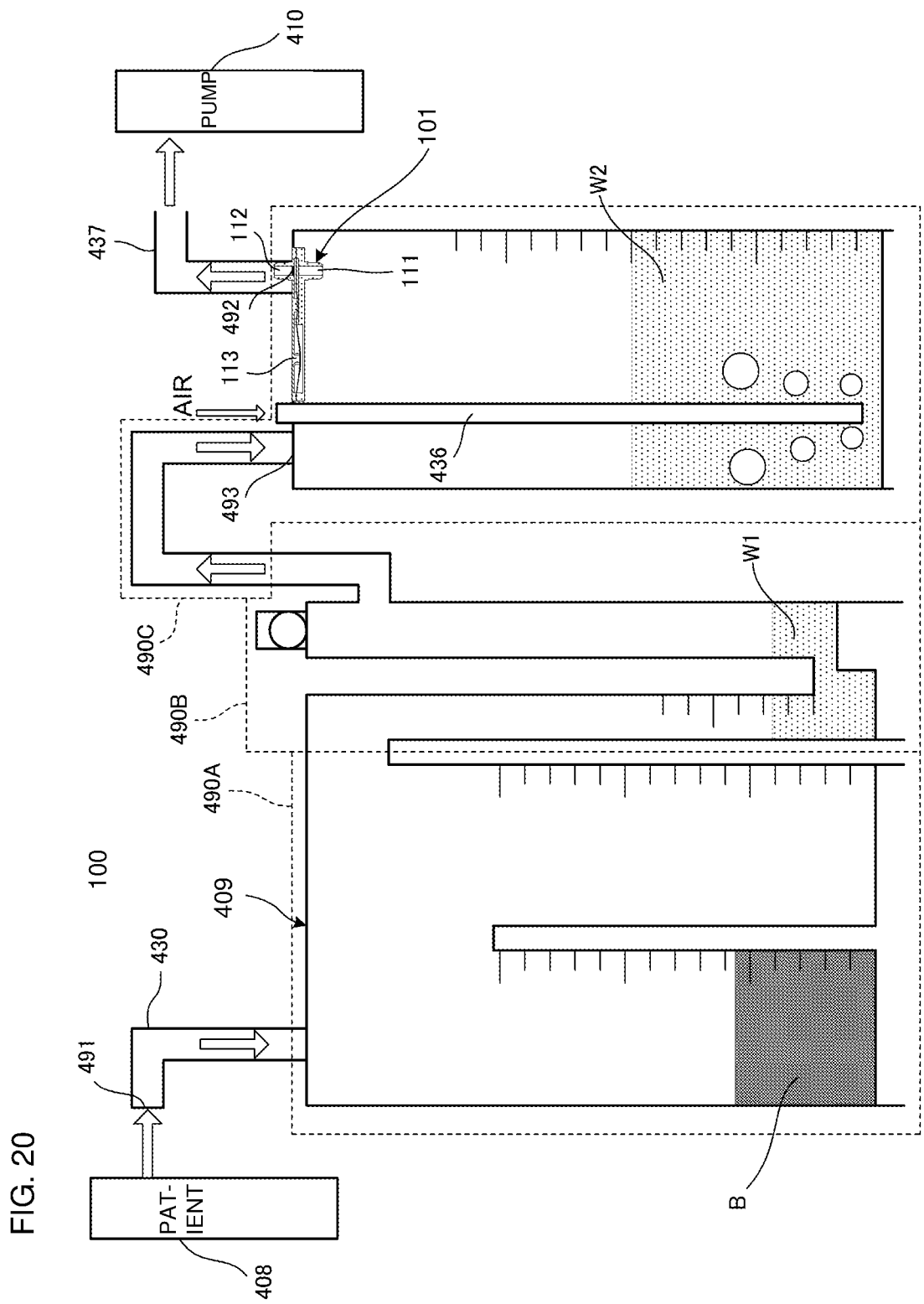
FIG. 20 is a cross-sectional view of a fluid control device 400 according to a fourth embodiment of the disclosure.

FIG. 20 is a cross-sectional view of the fluid control device 400 according to the fourth embodiment of the disclosure. Arrows in the FIG. 20 indicate fluid flow. The fluid control device 400 is a drainage that sucks liquid (for example, pleural effusion, blood, or the like). The fluid control device 400 includes a pump 410, an inhaler 409, and the valve 101.

The pump 410 is a desired pump and has a suction hole (not illustrated) for sucking the air and a discharge hole (not illustrated) for discharging the air.

The inhaler 409 is a so-called chest drain bag. The inhaler 409 has a first container 490A, a second container 490B, a third container 490C, a tube 430, a connection hole 492, and a tube 437. An inhalation port 491 at the end portion of the tube 430 is inserted into a thoracic cavity of a patient 408. The patient 408 is, for example, a human being or an animal.

The first container 490A is a so-called waste bottle. The first container 490A is connected to the inhalation port 491. The first container 490A stores therein liquid B (for example, pleural effusion, blood, or the like) of the patient 408, which has been sucked from the inhalation port 491.

The second container 490B is a so-called water-sealed bottle. The second container 490B is connected to the first container 490A. Water W1 is contained in the second container 490B. The second container 490B transmits the air in the water W1 and visualizes air flow.

The third container 490C is a so-called suction pressure control bottle. The third container 490C is connected to the second container 490B and the suction hole of the pump 410. Water W2 is contained in the third container 490C. A pipe 436 is inserted into the third container 490C and the end portion of the pipe 436 is dipped in the water W2. The third container 490C adjusts a suction pressure of the air that the pump 410 sucks based on the water level of the water W2 and the air flowing thereinto from the end portion of the pipe 436.

The valve 101 is attached to the inner surface of the third container 490C so as to close the connection hole 492 as an exit of the third container 490C. Any one of the first ventilation hole 111 and the second ventilation hole 112 in the valve 101 is connected to the connection hole 492 of the third container 490C.

With the above-described configuration, the inhalation port 491 communicates with the inside of the container 490A with the tube 430 interposed therebetween, the first ventilation hole 111 of the valve 101 communicates with a connection port 493 of the container 490C, and the second ventilation hole 112 of the valve 101 communicates with the suction hole (not illustrated) of the pump 410 with the tube 437 interposed therebetween. The third ventilation hole 113 of the valve 101 is opened to the atmosphere.

Then, air flow in the fluid control device 400 while the pump 410 is being driven is the same as the air flow in the fluid control device 100 illustrated in FIG. 10.

Air flow in the fluid control device 400 when driving of the pump 410 is stopped, a pressure in the container 490A reaches a maximum suction pressure of the pump 410, or a flow path is closed is also the same as the air flow in the fluid control device 100 illustrated in FIG. 11.

For example, the inhalation port 491 is closed when a tissue of a human body is sucked in a state in which there is no suction target. The closure of the inhalation port 491 lowers a flow rate and the pressure difference between the first region and the second region is 0. With this, the movable portion 120 automatically opens the third ventilation hole 113 to open the inhalation port 491 to the atmosphere.

Accordingly, also in the fluid control device 400, the valve 101 can perform the fluid suction operation and can passively release the pressure in the flow path to the atmosphere.

In the case of lung pneumothorax, it is said that a healing period can be shortened by stopping suction when a wound becomes small and the flow rate is lowered. Therefore, the valve 101 that automatically opens the inhalation port 491 is preferable for usage of treatment of lung pneumothorax.

Moreover, the inhaler 409 and the valve 101 can be disposable because the configuration of the valve 101 is simple and inexpensive. The valve 101 can therefore reduce maintenance cost of a hospital.

Furthermore, the fluid control device 400 including the valve 101 also provides the same effects.

Hereinafter, a fluid control device 450 according to a variation of the fourth embodiment of the disclosure will be described.

Figure 21:
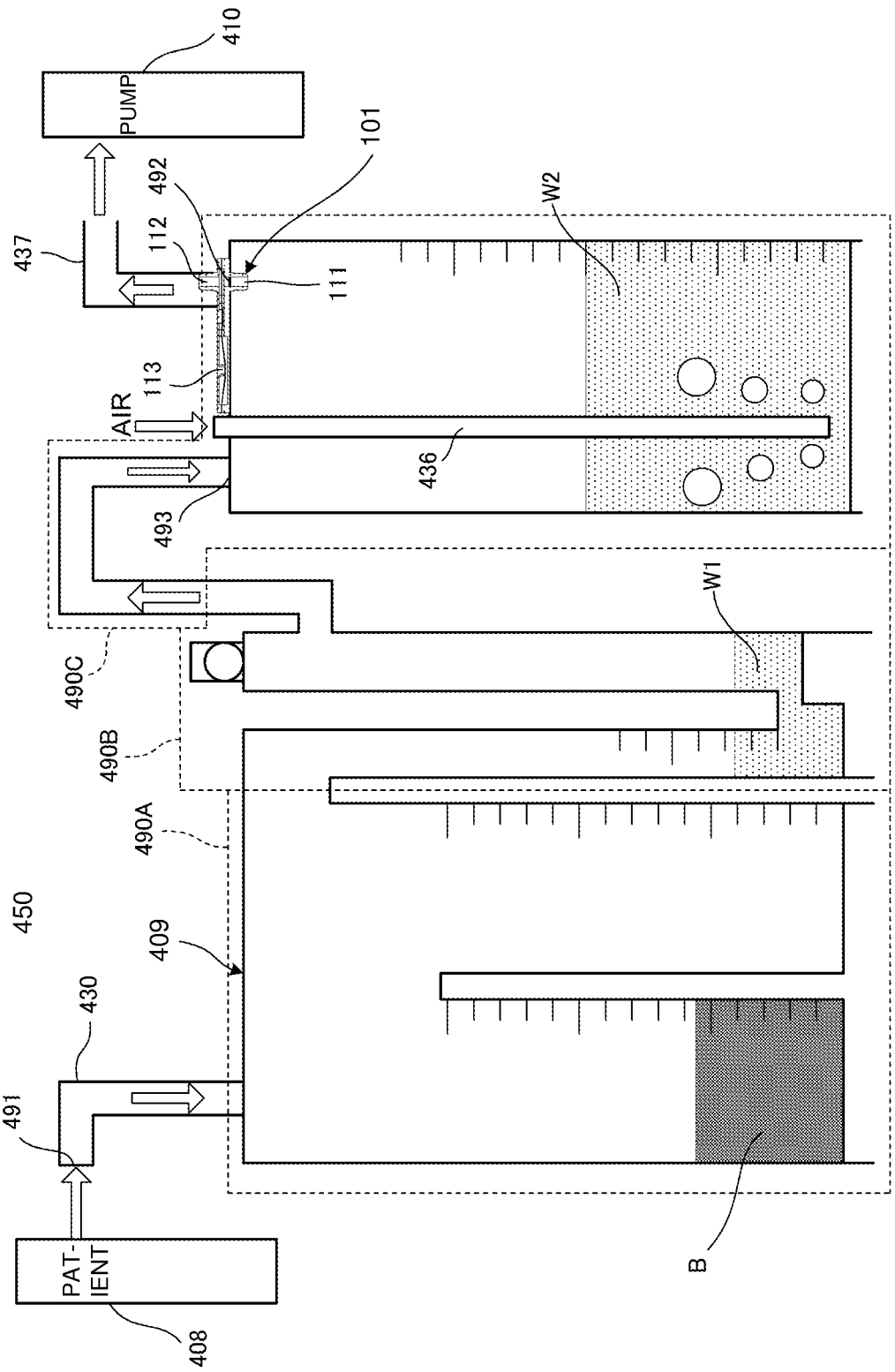
FIG. 21 is a cross-sectional view of a fluid control device 450 according to a variation of the fourth embodiment of the disclosure.

FIG. 21 is a cross-sectional view of the fluid control device 450 according to the variation of the fourth embodiment of the disclosure. The fluid control device 450 is different from the fluid control device 400 in a point that the valve 101 is provided in an outer side portion of the third container 490C so as to close the connection hole 492 of the third container 490C.

As will be described in detail, the first ventilation hole 111 of the valve 101 communicates with the connection hole 492 of the third container 490C. The second ventilation hole 112 of the valve 101 communicates with the suction hole (not illustrated) of the pump 410 with the tube 437 interposed therebetween. Other configurations thereof are the same and description thereof is therefore omitted.

Air flow in the fluid control device 450 while the pump 410 is being driven is the same as the air flow in the fluid control device 400 illustrated in FIG. 20. That is to say, air flow in the fluid control device 450 when driving of the pump 410 is stopped, the pressure in the container 490A reaches the maximum suction pressure of the pump 410, or the flow path is closed is also the same as the air flow in the fluid control device 400 illustrated in FIG. 20.

Accordingly, also in the fluid control device 450, the valve 101 can perform the fluid suction operation and can passively release the pressure in the flow path to the atmosphere. Furthermore, the fluid control device 450 including the valve 101 also provides the same effects.

In the fluid control device 400 illustrated in FIG. 20 or the fluid control device 450 illustrated in FIG. 21, when the patient 408 sneezes and so on, the pressure in the inhaler 409 is largely made into a negative pressure. Therefore, the fluid control device 400 or the fluid control device 450 is required to return the pressure in the inhaler 409 to a suction pressure immediately. The pressure in the inhaler 409 is also slightly reduced when the patient 408 normally breathes.

However, when the pressure in the inhaler 409 is returned to the suction pressure while involving frequent opening of the valve 101 every time the patient 408 normally breathes, the patient 408 is burdened.

The pressure with which the valve 101 is opened can be adjusted by adjusting the dimensions of the valve seat 139 and the valve seat 145. Therefore, each of the fluid control device 400 and the fluid control device 450 can make adjustment such that the valve 101 is not opened with normal breathing of the patient 408 whereas the valve 101 is opened only when the pressure in the inhaler 409 is largely reduced with a sneeze or the like.

Hereinafter, a fluid control device 500 according to a fifth embodiment of the disclosure will be described.

Figure 22:
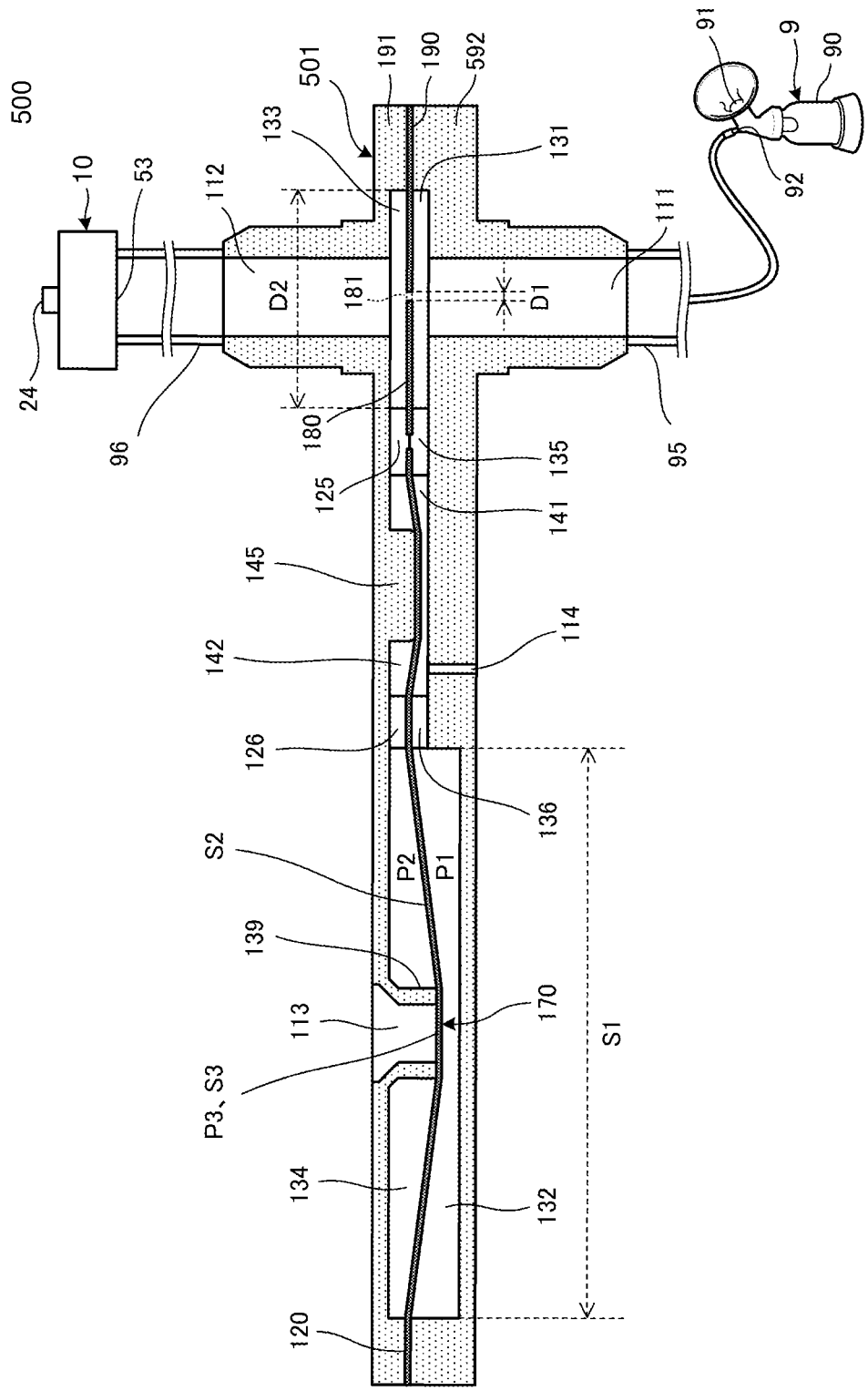
FIG. 22 is a cross-sectional view of a fluid control device 500 according to a fifth embodiment of the disclosure.

FIG. 22 is a cross-sectional view of the fluid control device 500 according to the fifth embodiment of the disclosure. The fluid control device 500 is different from the fluid control device 100 illustrated in FIG. 1 in a valve 501. The valve 501 is different from the valve 101 in a point that a second valve housing 592 has a fourth ventilation hole 114. The fourth ventilation hole 114 communicates with the first region. The diameter of the fourth ventilation hole 114 is smaller than the diameter of the first ventilation hole 111. Furthermore, the diameter of the fourth ventilation hole 114 is smaller than the diameter of the second ventilation hole 112. Other configurations of the fluid control device 500 are the same as those of the fluid control device 100 and description thereof is therefore omitted.

It should be noted that as described above, the first lower valve chamber 131, the communication path 135, the second lower valve chamber 141, the communication path 136, and the third lower valve chamber 132 correspond to the "first region" according to the disclosure. The first upper valve chamber 133, the communication path 125, the second upper valve chamber 142, the communication path 126, and the third upper valve chamber 134 correspond to the "second region" according to the disclosure. The valve seat 139 corresponds to the "valve seat" according to the disclosure.

Then, air flow in the fluid control device 500 will be described. The air flow in the fluid control device 500 is divided into a first stage before the pressure in the container 90 reaches the maximum suction pressure of the piezoelectric pump 10 after the driving of the piezoelectric pump 10 is started, a second stage before driving of the piezoelectric pump 10 is stopped after the pressure in the container 90 reaches the maximum suction pressure of the piezoelectric pump 10, and a third stage immediately after the driving of the piezoelectric pump 10 is stopped.

Initially, the air flow at the first stage will be described.

Figure 23:
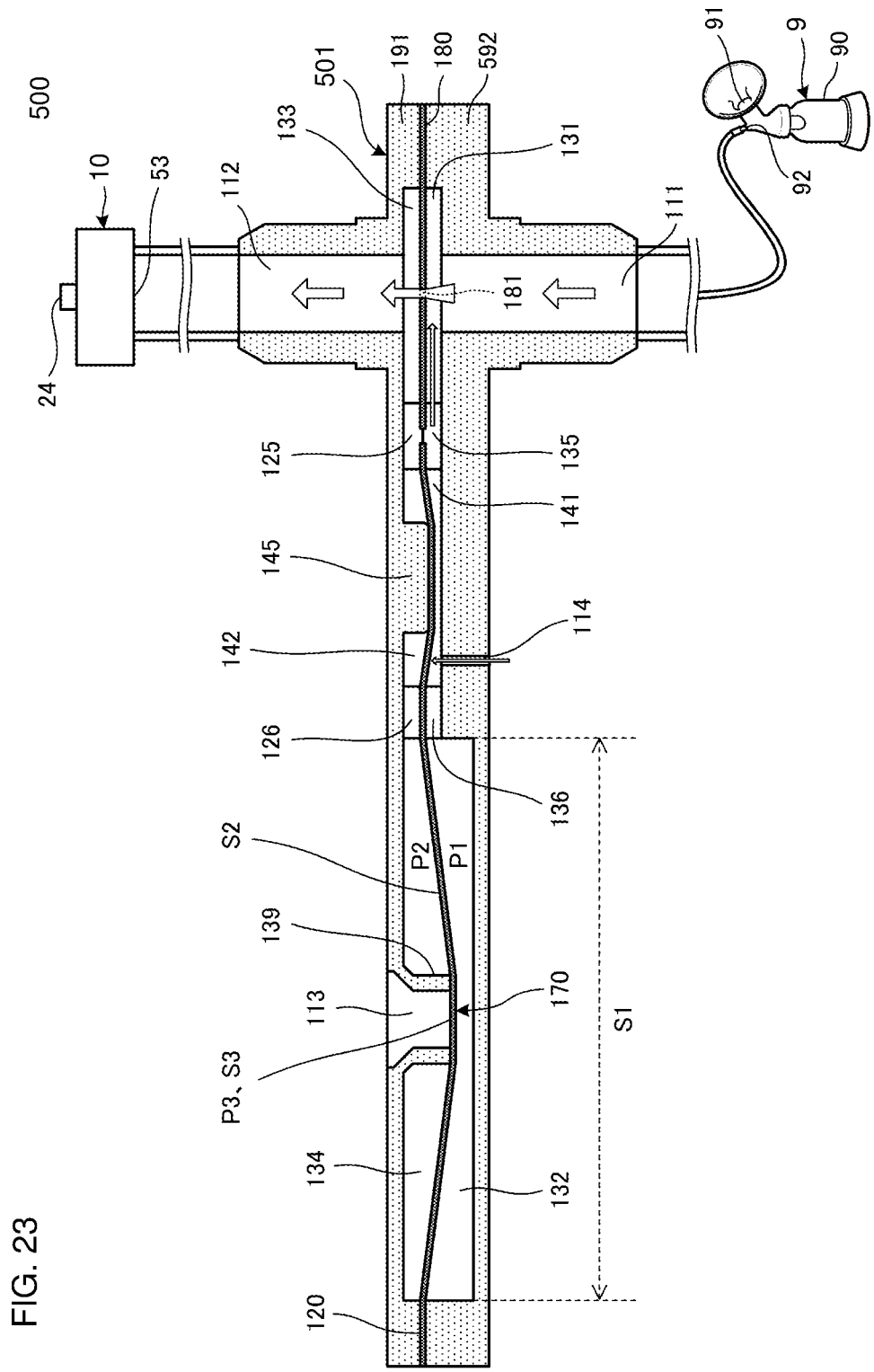
FIG. 23 is a descriptive view for explaining the air flow in the fluid control device 500 before the pressure in the container 90 reaches the maximum suction pressure after the driving of the piezoelectric pump 10 is started.

FIG. 23 is a descriptive view for explaining the air flow in the fluid control device 500 before the pressure in the container 90 reaches the maximum suction pressure after the driving of the piezoelectric pump 10 is started. Arrows in the drawing indicate the air flow.

First, a user attaches the inhalation port 91 of the inhaler 9 to, for example, the breast of the human being or the animal. The pressure in the container 90 before the piezoelectric pump 10 is driven is the atmospheric pressure. The fluid control device 500 turns the piezoelectric pump 10 ON when inhalation of liquid with the inhaler 9 is started.

When the piezoelectric pump 10 is driven, the air in the first upper valve chamber 133 is sucked into the piezoelectric pump 10 while passing through the second ventilation hole 112 and the suction hole 53. Then, the air in the piezoelectric pump 10 is discharged from the discharge hole 24.

In the fixed portion 180 of the valve body 190, although the first lower valve chamber 131 and the first upper valve chamber 133 communicate with each other with the first through-hole 181 interposed therebetween, pressure loss (flow path resistance) is generated with the first through-hole 181. For this reason, the pressure in the first lower valve chamber 131 becomes higher than the pressure in the first upper valve chamber 133.

Furthermore, in the exhaust valve 170, the pressure in the third lower valve chamber 132 is higher than the pressure in the third upper valve chamber 134. Therefore, the movable portion 120 closes the third ventilation hole 113 using a pressure difference between the third lower valve chamber 132 and the third upper valve chamber 134. The movable portion 120 thereby blocks communication between the second ventilation hole 112 and the third ventilation hole 113.

That is to say, when the pressure in the first region is higher than the pressure in the second region, the valve body 190 blocks communication between the second ventilation hole 112 and the third ventilation hole 113 and communicates the first ventilation hole 111 and the second ventilation hole 112 with each other with the first through-hole 181 interposed therebetween.

Therefore, the air flows to the second ventilation hole 112 from the first ventilation hole 111 while passing through the first through-hole 181. The air flowed out from the second ventilation hole 112 is sucked into the piezoelectric pump 10 while passing through the suction hole 53 to be discharged from the discharge hole 24.

As a result, the air in the container 90 of the inhaler 9 is discharged to the second lower valve chamber 141 of the valve 501 from the connection hole 92 while passing through the first ventilation hole 111. With this, the pressure (air pressure) in the container 90 becomes lower than the atmospheric pressure and is made into a negative pressure.

Therefore, the inhaler 9 can inhale liquid (for example, breast milk or the like) at the outside of the container 90 into the container 90 from the inhalation port 91. The inhaler 9 stores the liquid in the container 90 and discharges the air in the container 90 from the connection hole 92.

Herein, in the fluid control device 500, the small volume of air is sucked into the valve 501 from the outside of the valve 501 while passing through the fourth ventilation hole 114. This decreases a flow rate of the air that is sucked from the container 90 in comparison with the fluid control device 100, in the fluid control device 500.

However, the diameter of the fourth ventilation hole 114 is finer than the diameter of the first ventilation hole 111 and less influence thereby is given. Therefore, the air is mainly sucked into the valve 501 from the first ventilation hole 111 and the air flows into the piezoelectric pump 10 from the container 90. With this, relations of P2<P1 and (S1−S3)×(P1−P2)>S3×(P3−P1) are satisfied in the exhaust valve 170.

Meanwhile, when the piezoelectric pump 10 is continuously driven for a long period of time in the fluid control device 100 illustrated in FIG. 10, the air in the container 90 is sufficiently reduced and the pressure in the container 90 reaches the maximum suction pressure. This eliminates the pressure difference between P1 and P2. As a result, there is the possibility that the third ventilation hole 113 is opened, the air flows into the second region from the third ventilation hole 113, and the relation of P2<P1 cannot be maintained. That is to say, the fluid control device 100 cannot possibly maintain sufficient suction force.

The air flow at the second stage in the fluid control device 500 will be described.

Figure 24:
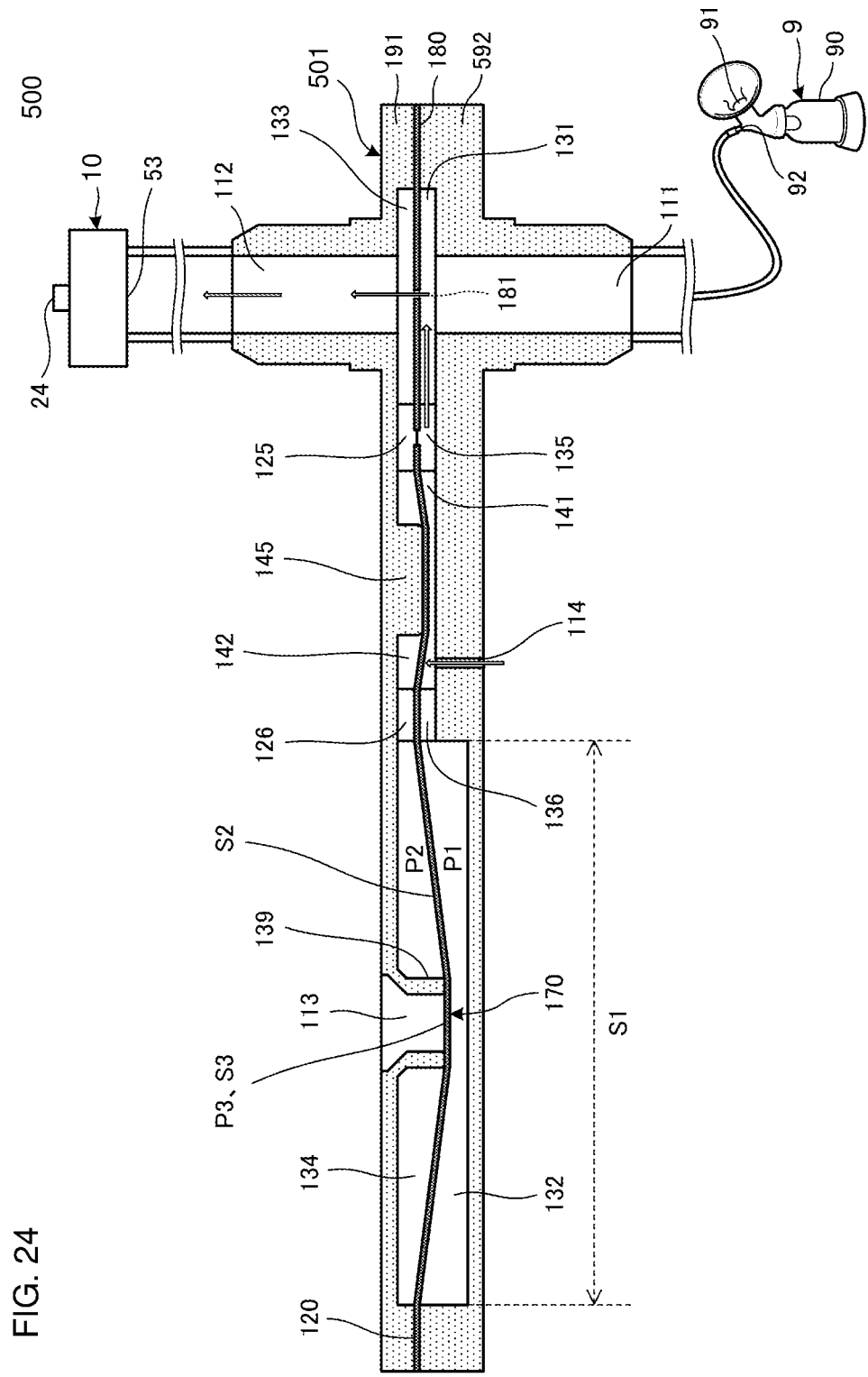
FIG. 24 is a descriptive view for explaining the air flow in the fluid control device 500 before driving of the piezoelectric pump 10 is stopped after the pressure in the container 90 reaches the maximum suction pressure.

FIG. 24 is a descriptive view for explaining the air flow in the fluid control device 500 before driving of the piezoelectric pump 10 is stopped after the pressure in the container 90 reaches the maximum suction pressure. Arrows in the drawing indicate the air flow.

At the second stage of the fluid control device 500, the air is sucked from the fourth ventilation hole 114, and flows to the piezoelectric pump 10 while passing through the first through-hole 181. Therefore, the valve 501 can keep the difference between P1 and P2 at the time of suction to be equal to or higher than a constant value with the fourth ventilation hole 114. The relations of P2<P1 and (S1−S3)×(P1−P2)>S3×(P3−P1) are maintained in the exhaust valve 170.

As described above, the valve 501 can maintain a state in which the third ventilation hole 113 is closed. That is to say, the valve 501 can maintain a decompressed state of the container 90 while the piezoelectric pump 10 is being continuously driven.

Subsequently, the air flow at the third stage will be described.

Figure 25:
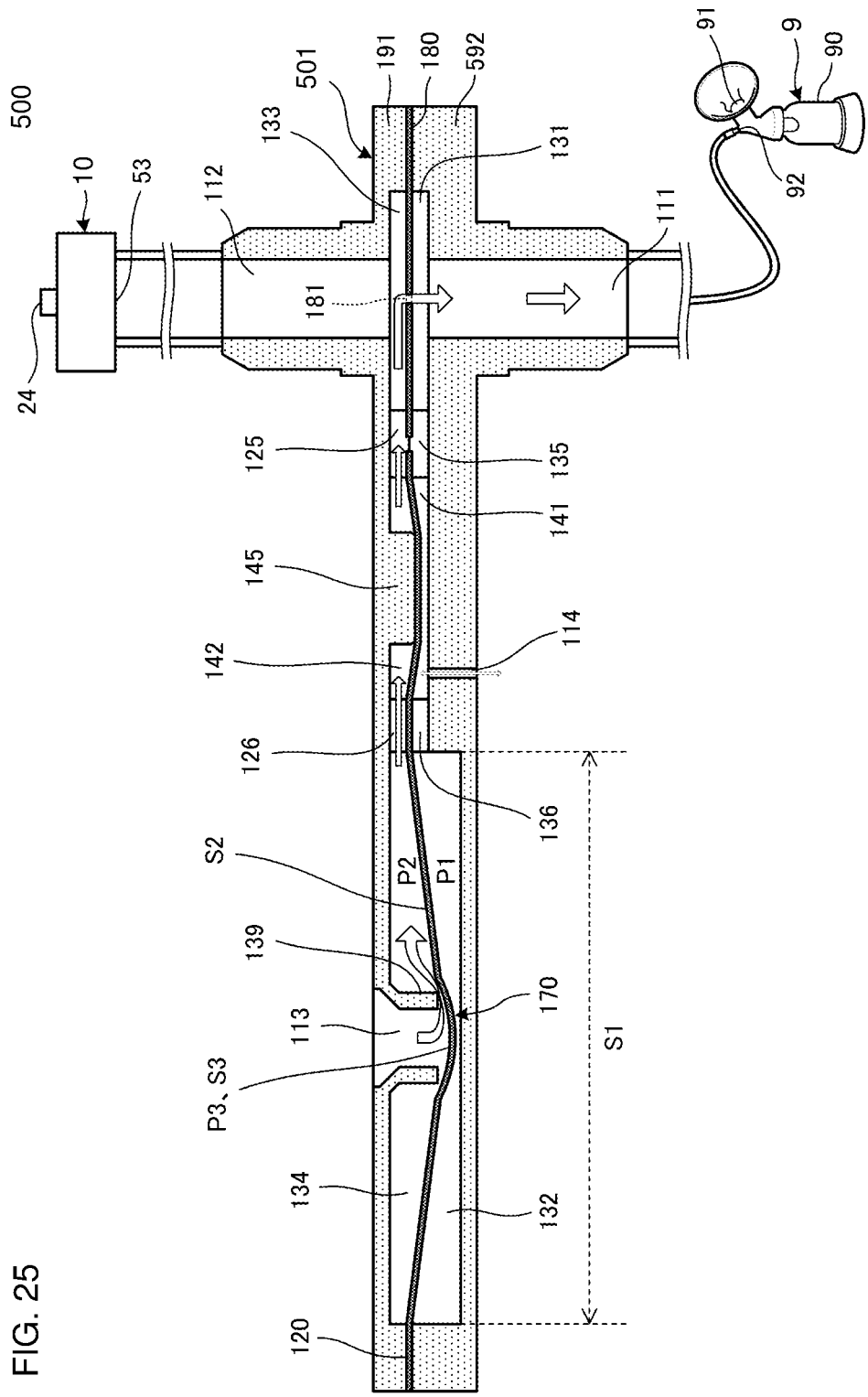
FIG. 25 is a descriptive view for explaining air flow in the fluid control device 500 immediately after the driving of the piezoelectric pump 10 is stopped.

FIG. 25 is a descriptive view for explaining the air flow in the fluid control device 500 immediately after the driving of the piezoelectric pump 10 is stopped. Arrows in the drawing indicate the air flow.

When inhalation of the liquid by the inhaler 9 is finished, the fluid control device 500 turns the piezoelectric pump 10 OFF to stop driving of the piezoelectric pump 10. In this case, the pressure in the first lower valve chamber 131 becomes equal to the pressure in the first upper valve chamber 133 with the first through-hole 181. It should be noted that the pressure of the inside of the valve 501 is lower than the atmospheric pressure. Therefore, the small volume of air is sucked into the valve 501 from the outside of the valve 501 while passing through the fourth ventilation hole 114.

However, the diameter of the fourth ventilation hole 114 is finer than the diameter of the second ventilation hole 112 and less influence thereby is given. Therefore, the fine volume of air mainly flows into the piezoelectric pump 10 from the discharge hole 24 of the piezoelectric pump 10, and flows into the second region while passing through the suction hole 53 and the second ventilation hole 112.

As a result, in the exhaust valve 170, the pressure in the third lower valve chamber 132 becomes equal to the pressure in the third upper valve chamber 134. That is to say, relations of P2=P1 and (S1−S3)×(P1−P2)<S3×(P3−P1) are satisfied in the exhaust valve 170. Therefore, the movable portion 120 is separated from the valve seat 139 to open the third ventilation hole 113 in the exhaust valve 170.

That is to say, in the valve 501, when the pressure in the first region is equal to or lower than the pressure in the second region, the valve body 190 communicates the second ventilation hole 112 and the third ventilation hole 113 with each other and communicates the first ventilation hole 111 and the second ventilation hole 112 with each other with the first through-hole 181 interposed therebetween.

Therefore, as illustrated in FIG. 25, the air flows in from the third ventilation hole 113, and flows to the first lower valve chamber 131 while passing through the third upper valve chamber 134, the communication path 126, the second upper valve chamber 142, the first upper valve chamber 133, and the first through-hole 181.

In this case, the small volume of air flowed to the second lower valve chamber 141 from the first lower valve chamber 131 flows to the outside of the valve 501 from the inside of the valve 501 while passing through the fourth ventilation hole 114. However, the diameter of the fourth ventilation hole 114 is finer than the diameter of the first ventilation hole 111 and less influence thereby is given. Therefore, the air flowed to the first lower valve chamber 131 mainly flows into the container 90 from the first ventilation hole 111 while passing through the tube.

The pressure (air pressure) in the container 90 is thereby increased to be returned to the atmospheric pressure. This enables the inhalation port 91 of the inhaler 9 to be easily detached from the breast of the human being or the animal.

As described above, the valve 501 in the embodiment opens and closes the third ventilation hole 113 with the pressure difference between the first region and the second region by the flow path resistance of the first through-hole 181.

Accordingly, the valve 501 in the embodiment can perform the fluid suction operation and can passively release the pressure in the flow path to the atmosphere without providing special components such as a pressure sensor, a flowmeter, and an electromagnetic valve.

Unlike the electromagnetic valve, the valve 501 passively opens and closes the valve as described above. This enables the valve 501 to reduce power consumption in comparison with the electromagnetic valve. The valve 501 is therefore preferable for a breast pump that is required to be driven with less power consumption. Furthermore, the fluid control device 500 including the valve 501 in the embodiment also provides the same effects.

Hereinafter, a fluid control device 600 according to a sixth embodiment of the disclosure will be described.

Figure 26:
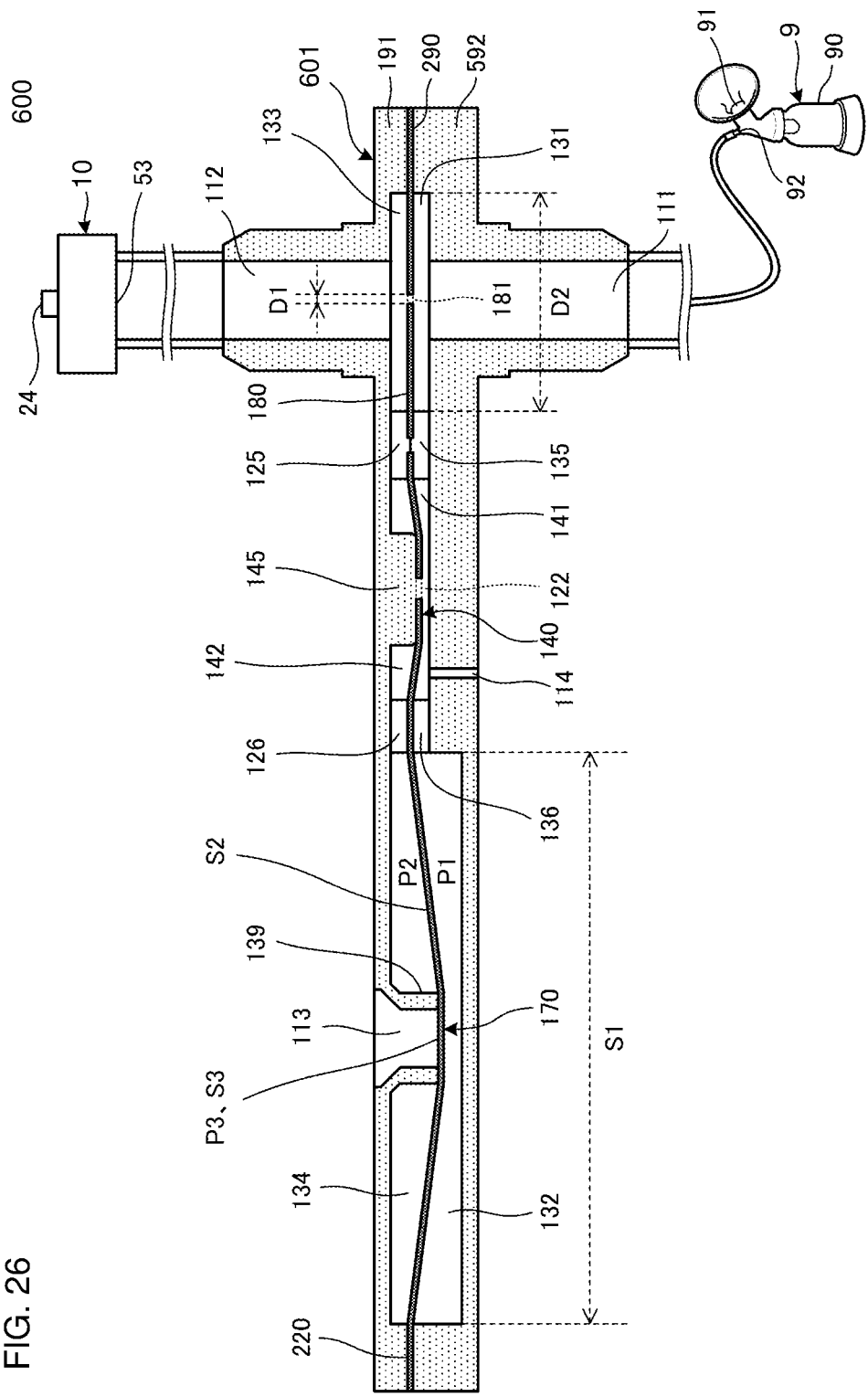
FIG. 26 is a cross-sectional view of a fluid control device 600 according to a sixth embodiment of the disclosure.

FIG. 26 is a cross-sectional view of the fluid control device 600 according to the sixth embodiment of the disclosure. The fluid control device 600 is different from the fluid control device 200 illustrated in FIG. 15 in a valve 601. The valve 601 is different from the valve 201 in a point that a second valve housing 592 has the above-described fourth ventilation hole 114. Other configurations of the fluid control device 600 are the same as those of the fluid control device 200 and description thereof is therefore omitted.

Furthermore, the fluid control device 600 is different from the fluid control device 500 illustrated in FIG. 22 in a point that the movable portion 220 of the valve body 290 included in the valve 601 has the above-described second through-hole 122. As described above, the check valve 140 is configured by the second lower valve chamber 141, the second upper valve chamber 142, the valve seat 145, and a region of the valve body 290, which faces the second lower valve chamber 141 and the second upper valve chamber 142. Other configurations of the fluid control device 600 are the same as those of the fluid control device 500 and description thereof is therefore omitted.

Then, air flow in the fluid control device 600 will be described. The air flow in the fluid control device 600 is divided into a first stage before the pressure in the container 90 reaches the maximum suction pressure of the piezoelectric pump 10 after the driving of the piezoelectric pump 10 is started, a second stage before the driving of the piezoelectric pump 10 is stopped after the pressure in the container 90 reaches the maximum suction pressure of the piezoelectric pump 10, and a third stage immediately after the driving of the piezoelectric pump 10 is stopped.

First, the air flow at the first stage will be described.

Figure 27:
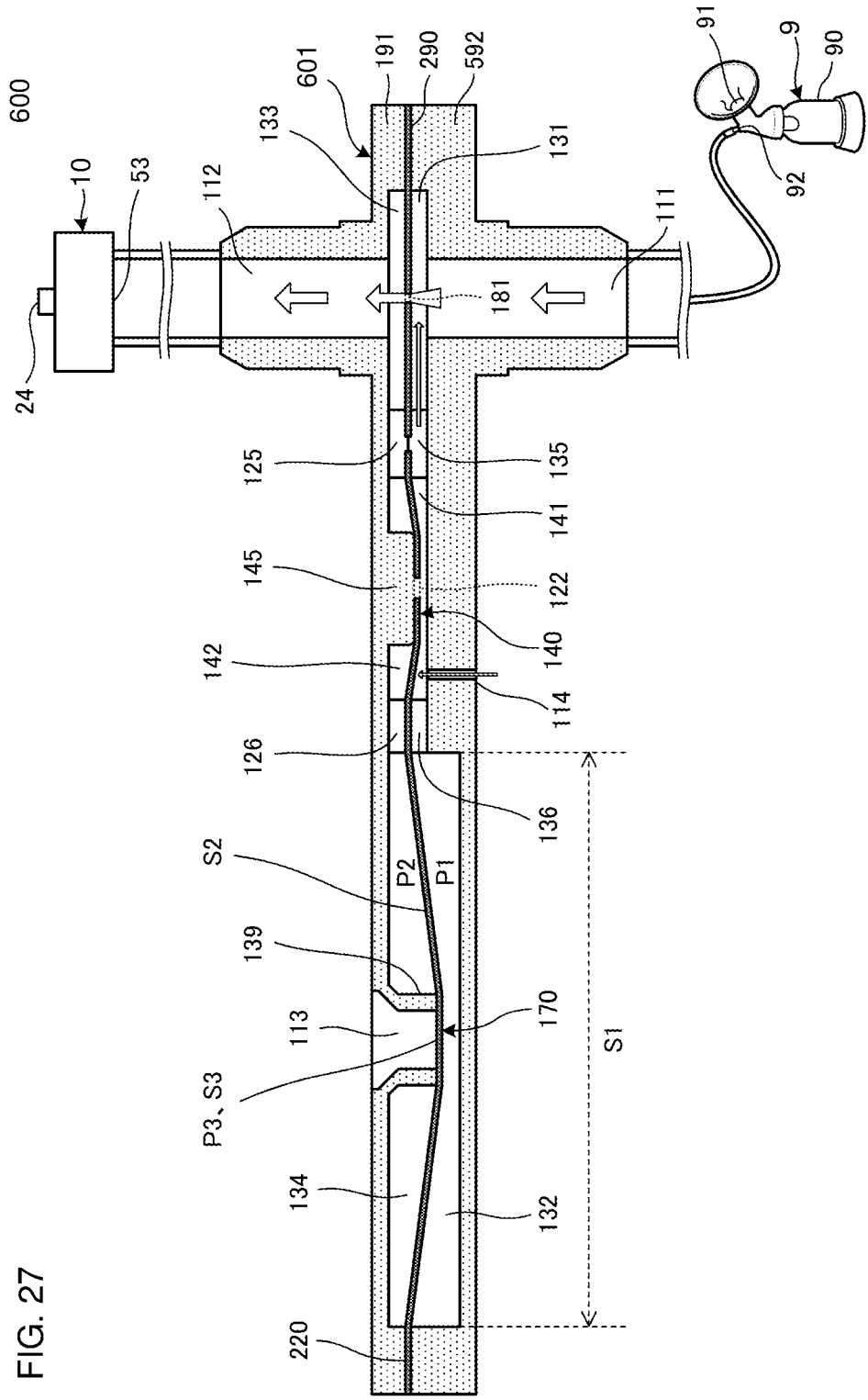
FIG. 27 is a descriptive view for explaining the air flow in the fluid control device 600 before the pressure in the container 90 reaches the maximum suction pressure after the driving of the piezoelectric pump 10 is started.

FIG. 27 is a descriptive view for explaining the air flow in the fluid control device 600 before the pressure in the container 90 reaches the maximum suction pressure after the driving of the piezoelectric pump 10 is started.

The air flow at the first stage in the fluid control device 600 is the same as the air flow at the first stage in the fluid control device 500 (see FIG. 23). In the check valve 140, the pressure in the second lower valve chamber 141 is higher than the pressure in the second upper valve chamber 142. Therefore, the state in which the circumference of the second through-hole 122 in the movable portion 220 makes contact with the valve seat 145 is maintained.

Then, the air flow at the second stage will be described.

Figure 28:
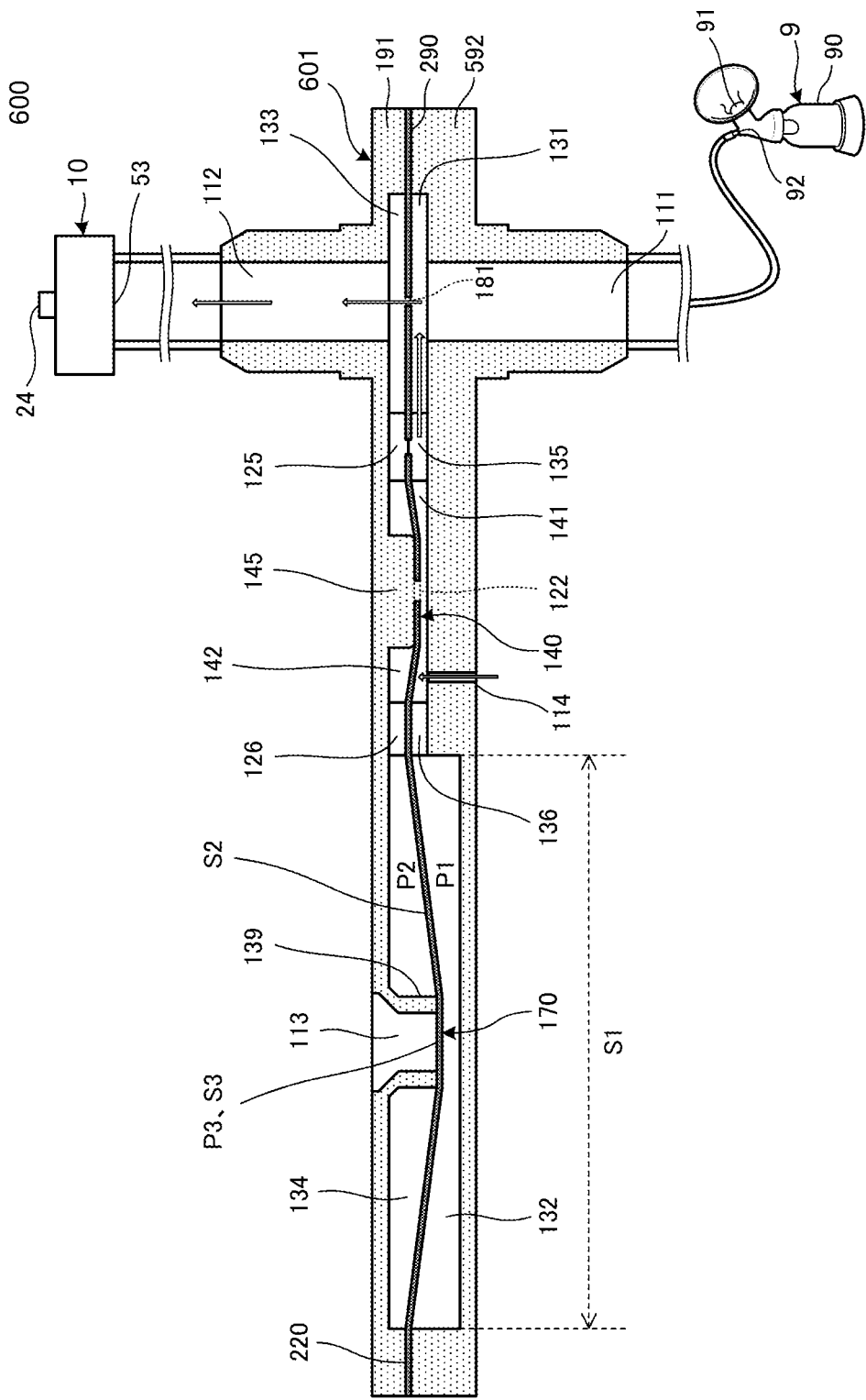
FIG. 28 is a descriptive view for explaining the air flow in the fluid control device 600 before driving of the piezoelectric pump 10 is stopped after the pressure in the container 90 reaches the maximum suction pressure.

FIG. 28 is a descriptive view for explaining the air flow in the fluid control device 600 before driving of the piezoelectric pump 10 is stopped after the pressure in the container 90 reaches the maximum suction pressure.

The air flow at the second stage in the fluid control device 600 is the same as the air flow at the second stage in the fluid control device 500 (see FIG. 24). In the check valve 140, the pressure in the second lower valve chamber 141 is higher than the pressure in the second upper valve chamber 142. Therefore, the state in which the circumference of the second through-hole 122 in the movable portion 220 makes contact with the valve seat 145 is maintained.

Also at the second stage in the fluid control device 600, the air is sucked from the fourth ventilation hole 114, and flows to the piezoelectric pump 10 while passing through the first through-hole 181. Therefore, the valve 501 can keep the difference between P1 and P2 at the time of suction to be equal to or higher than a constant value with the fourth ventilation hole 114. The relations of $P2<P1$ and $(S1-S3)\times(P1-P2)>S3\times(P3-P1)$ are satisfied in the exhaust valve 170.

As described above, the valve 601 can maintain a state in which the third ventilation hole 113 is closed. That is to say, the valve 601 can maintain a decompressed state of the container 90 while the piezoelectric pump 10 is being continuously driven.

Subsequently, the air flow at the third stage will be described.

Figure 29:
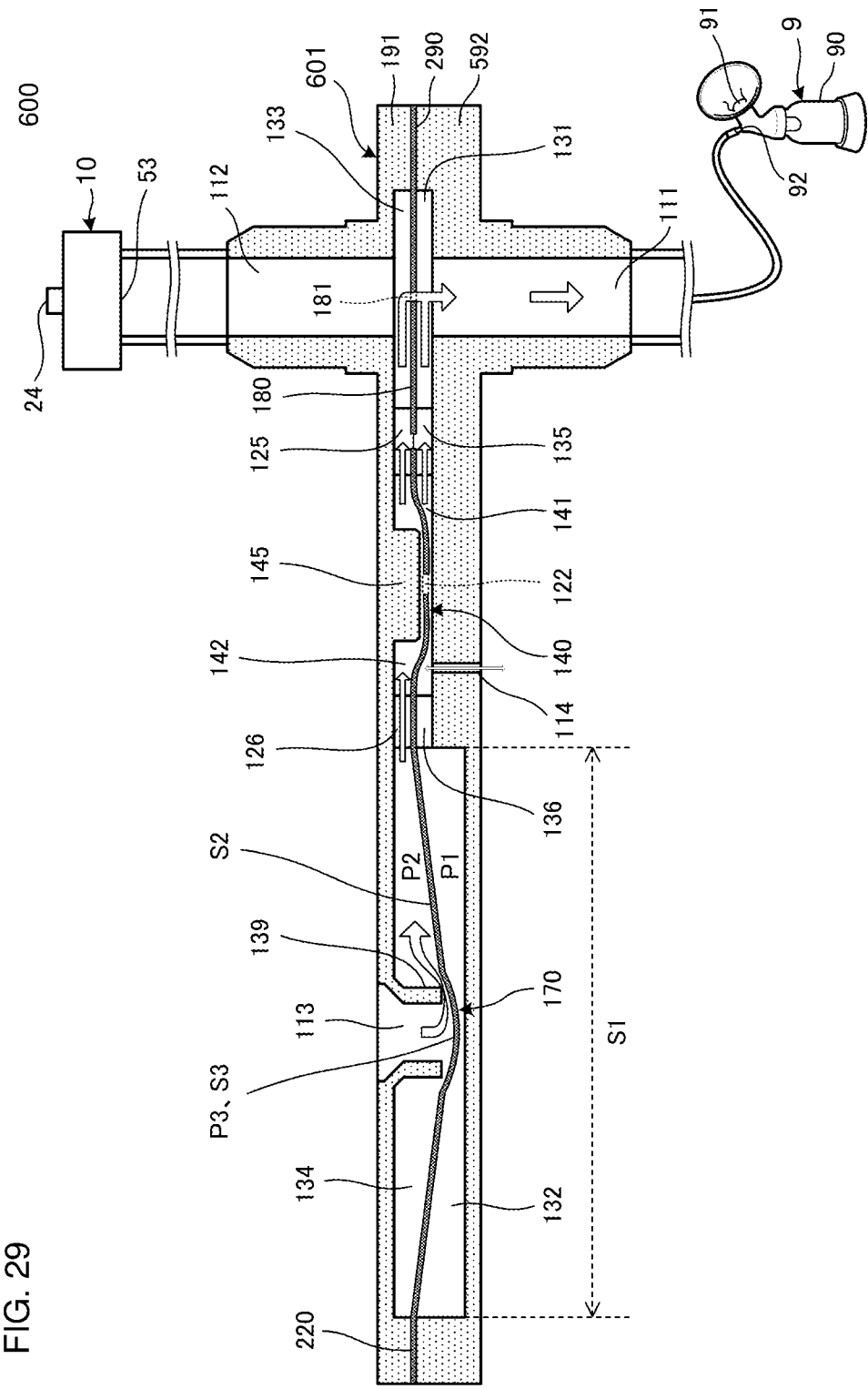
FIG. 29 is a descriptive view for explaining air flow in the fluid control device 600 immediately after the driving of the piezoelectric pump 10 is stopped.

FIG. 29 is a descriptive view for explaining the air flow in the fluid control device 600 immediately after the driving of the piezoelectric pump 10 is stopped.

When inhalation of the liquid by the inhaler 9 is finished, the fluid control device 600 turns the piezoelectric pump 10 OFF to stop driving of the piezoelectric pump 10. In this case, the pressure in the first lower valve chamber 131 becomes equal to the pressure in the first upper valve chamber 133 with the first through-hole 181. It should be noted that the inside of the valve 601 is lower than the atmospheric pressure. Therefore, the small volume of air is sucked into the valve 601 from the outside of the valve 601 while passing through the fourth ventilation hole 114.

However, the diameter of the fourth ventilation hole 114 is finer than the diameter of the second ventilation hole 112 and less influence thereby is given. Therefore, the fine volume of air mainly flows into the piezoelectric pump 10 from the discharge hole 24 of the piezoelectric pump 10, and flows into the second region while passing through the suction hole 53 and the second ventilation hole 112.

As a result, in the exhaust valve 170, the pressure in the third lower valve chamber 132 becomes equal to the pressure in the third upper valve chamber 134. That is to say, relations of $P2=P1$ and $(S1-S3)\times(P1-P2)<S3\times(P3-P1)$ are satisfied in the exhaust valve 170. Therefore, the movable portion 120 is separated from the valve seat 139 to open the third ventilation hole 113 in the exhaust valve 170.

That is to say, in the valve 601, when the pressure in the first region is equal to or lower than the pressure in the second region, the valve body 190 communicates the second ventilation hole 112 and the third ventilation hole 113 with each other and communicates the first ventilation hole 111 and the second ventilation hole 112 with each other with the first through-hole 181 interposed therebetween.

Therefore, as illustrated in FIG. 29, the air flows in from the third ventilation hole 113, and flows to the first lower valve chamber 131 while passing through the third upper valve chamber 134, the communication path 126, the second upper valve chamber 142, the first upper valve chamber 133, and the first through-hole 181.

Furthermore, in the check valve 140, the pressure in the second lower valve chamber 141 is lower than the pressure in the second upper valve chamber 142 after the exhaust valve 170 is opened. Accordingly, the circumference of the second through-hole 122 in the movable portion 220 is separated from the valve seat 145 to communicate the first ventilation hole 111 and the second region with each other. The air therefore flows to the first lower valve chamber 131 from the third ventilation hole 113 while passing through the second through-hole 122 and the second lower valve chamber 141.

That is to say, in the valve 601, the air flows to the first ventilation hole 111 from the third ventilation hole 113 while passing through both of the first through-hole 181 and the second through-hole 122.

With the air flow, the air rapidly flows into the container 90 from the first ventilation hole 111. The pressure (air pressure) in the container 90 is thereby increased to be returned to the atmospheric pressure rapidly. This enables the inhalation port 91 of the inhaler 9 to be easily detached from the breast of the human being or the animal.

Accordingly, the valve 601 can perform the fluid suction operation and can passively release the pressure in the flow path to the atmosphere for a short period of time. Unlike the electromagnetic valve, the valve 601 passively opens and closes the valve as described above. This enables the valve 601 to reduce power consumption in comparison with the electromagnetic valve. The valve 601 is therefore preferable for a breast pump that is required to be driven with less power consumption. Furthermore, the fluid control device 600 including the valve 601 in the embodiment also provides the same effects.

It should be noted that the air flow at the third stage causes a part of the air flowed to the second lower valve chamber 141 from the third ventilation hole 113 while passing through the second through-hole 122 to be flown out to the outside of the valve 601 from the inside of the valve 601 while passing through the fourth ventilation hole 114. However, the diameter of the fourth ventilation hole 114 is smaller than the diameter of the first ventilation hole 111 and less influence thereby is given. Therefore, the air flowed to the first lower valve chamber 131 mainly flows into the container 90 from the first ventilation hole 111 while passing through the tube.

OTHER EMBODIMENTS

It should be noted that although in the above-described embodiments, the air is used as a sort of the fluid, the fluid is not limited to the air and liquids or gases other than the air can be applied to the fluid.

Furthermore, although the inhaler inhales the liquid as an example in the above-described embodiments, a target to be inhaled may not be the liquid (for example, may be a gel-like material).

Although the number of through-holes is one in the above-described embodiments, the number of through-holes is not limited thereto. In practice, the number of through-holes may be equal to or more than two.

Although the piezoelectric pump 10 includes the actuator that vibrates in the bending manner with expansion and contraction of the piezoelectric element 40 in the above-described embodiments, the piezoelectric pump 10 is not limited thereto. For example, the piezoelectric pump 10 may include an actuator that vibrates in a bending manner with electromagnetic driving.

Moreover, although the piezoelectric pump 10 in the above-described embodiments includes a unimorph actuator that vibrates in a bending manner, the piezoelectric pump 10 may include a biomorph actuator that vibrates in a bending manner by bonding the piezoelectric elements to both surfaces of the vibration plate.

Although the piezoelectric element 40 is made of PZT-based ceramic in the above-described embodiments, the piezoelectric element 40 is not limited to be made thereof. For example, the piezoelectric element 40 may be made of a piezoelectric material of non-lead-based piezoelectric ceramic such as sodium potassium niobate-based ceramic and alkali niobate-based ceramic.

Finally, it should be considered that the descriptions of the above-described embodiments are exemplary in all of points and are non-limiting. The range of the disclosure is indicated not by the above-described embodiments but by the scope of the disclosure. Furthermore, the scope of the disclosure is intended to encompass all meanings equivalent to the scope of the disclosure and all of changes within the scope.

9 INHALER
10 PIEZOELECTRIC PUMP
17 OUTER HOUSING
18 NOZZLE
24 DISCHARGE HOLE
31 VENTILATION PATH
36 PUMP CHAMBER
37 TOP PLATE
38 SIDE PLATE
39 VIBRATION PLATE
40 PIEZOELECTRIC ELEMENT
42 CAP
45 VENTILATION HOLE
52 PROJECTION
53 SUCTION HOLE
55A TO 55D CUTOUT
56A TO 56D SCREW HOLE
61 CENTER PORTION
62 PROJECTION
63, 72 EXTERNAL TERMINAL
70 ELECTRODE CONDUCTION PLATE
73 INTERNAL TERMINAL
90 CONTAINER
91 INHALATION PORT
92 CONNECTION HOLE
95, 96 TUBE
100, 200, 300, 400, 450, 500, 600 FLUID CONTROL DEVICE
101, 201, 301, 501, 601 VALVE
111 FIRST VENTILATION HOLE
112 SECOND VENTILATION HOLE
113 THIRD VENTILATION HOLE
114 FOURTH VENTILATION HOLE
120 MOVABLE PORTION
122 SECOND THROUGH-HOLE
125, 126 COMMUNICATION PATH
131 FIRST LOWER VALVE CHAMBER
132 THIRD LOWER VALVE CHAMBER
133 FIRST UPPER VALVE CHAMBER
134 THIRD UPPER VALVE CHAMBER
135, 136 COMMUNICATION PATH
139 VALVE SEAT

140 CHECK VALVE
141 SECOND LOWER VALVE CHAMBER
142 SECOND UPPER VALVE CHAMBER
145 VALVE SEAT
170 EXHAUST VALVE
180 FIXED PORTION
181 FIRST THROUGH-HOLE
190 VALVE BODY
191 FIRST VALVE HOUSING
192 SECOND VALVE HOUSING
220 MOVABLE PORTION
290 VALVE BODY
309 INHALER
310 PUMP
315 PRESSURE GAUGE
350 FILTER
353 SUCTION HOLE
390 CONTAINER
391 INHALATION PORT
392 CONNECTION HOLE
393 HOUSING
394, 395, 396 TUBE
408 PATIENT
409 INHALER
410 PUMP
430 TUBE
436 PIPE
437 TUBE
490A FIRST CONTAINER
490B SECOND CONTAINER
490C THIRD CONTAINER
491 INHALATION PORT
492 CONNECTION HOLE
493 CONNECTION PORT
592 SECOND VALVE HOUSING

The invention claimed is:

1. A valve comprising:
a valve housing having a first ventilation hole, a second ventilation hole, and a third ventilation hole; and
a valve body comprising a first region communicating with the first ventilation hole and a second region communicating with the second ventilation hole in the valve housing,
wherein the valve body has a fixed portion with a first through-hole communicating the first region and the second region with each other and a movable portion switching a communication state between the second ventilation hole and the third ventilation hole,
the valve body is fixed to the valve housing such that:
when a pressure in the first region is higher than a pressure in the second region, the valve body blocks communication between the second ventilation hole and the third ventilation hole and communicates the first ventilation hole and the second ventilation hole with each other with the first through-hole interposed therebetween, and
when the pressure in the first region is equal to or lower than the pressure in the second region, the valve body communicates the second ventilation hole and the third ventilation hole with each other and communicates the first ventilation hole and the second ventilation hole with each other with the first through-hole interposed therebetween.

2. The valve according to claim 1,
wherein the movable portion makes contact with or is separated from a first portion as a part of the valve housing with a pressure difference between the first region and the second region to switch the communication state.

3. The valve according to claim 2,
wherein the valve housing has, in the first portion, the third ventilation hole and a valve seat projecting to the movable portion from a circumference of the third ventilation hole in the second region, and
the valve body is fixed to the valve housing such that the movable portion makes contact with the valve seat.

4. The valve according to claim 3,
wherein the movable portion has a second through-hole communicating the first region and the second region with each other when the second ventilation hole communicates with the first ventilation hole and the third ventilation hole.

5. The valve according to claim 3,
wherein the valve housing has a filter which passes gas and prevents liquid from passing.

6. The valve according to claim 2,
wherein the movable portion has a second through-hole communicating the first region and the second region with each other when the second ventilation hole communicates with the first ventilation hole and the third ventilation hole.

7. The valve according to claim 2,
wherein the valve housing has a filter which passes gas and prevents liquid from passing.

8. The valve according to claim 1,
wherein the movable portion has a second through-hole communicating the first region and the second region with each other when the second ventilation hole communicates with the first ventilation hole and the third ventilation hole.

9. The valve according to claim 8,
wherein the movable portion makes contact with or is separated from a second portion as a part of the valve housing to close or open the second through-hole, and
the valve body is fixed to the valve housing such that:
when the pressure in the first region is higher than the pressure in the second region, the valve body closes the second through-hole, and
when the pressure in the first region is equal to or lower than the pressure in the second region, the valve body opens the second through-hole to communicate the first ventilation hole, the second ventilation hole, and the third ventilation hole with each other with the first through-hole and the second through-hole interposed therebetween.

10. The valve according to claim 9,
wherein the valve housing has a filter which passes gas and prevents liquid from passing.

11. The valve according to claim 8,
wherein the valve housing has a filter which passes gas and prevents liquid from passing.

12. The valve according to claim 1,
wherein the valve housing has a fourth ventilation hole communicating with the first region.

13. The valve according to claim 12,
wherein a cross-sectional area of the fourth ventilation hole is smaller than a cross-sectional area of the first ventilation hole.

14. The valve according to claim 13,
wherein the valve housing has a filter which passes gas and prevents liquid from passing.

15. The valve according to claim 12,
wherein a cross-sectional area of the fourth ventilation hole is larger than a cross-sectional area of the first ventilation hole.

16. The valve according to claim 12,
wherein the valve housing has a filter which passes gas and prevents liquid from passing.

17. The valve according to claim 1,
wherein the valve housing has a filter which passes gas and prevents liquid from passing.

18. A fluid control device comprising:
the valve according to claim 1;
a pump having a suction hole and sucking gas from the suction hole; and
an inhaler having a inhalation port for inhaling fluid,
wherein the first ventilation hole of the valve communicates with a part of the inhaler, and
the second ventilation hole of the valve communicates with the suction hole of the pump.

19. The fluid control device according to claim 18,
wherein the inhaler inhales breast milk from the inhalation port.

20. The fluid control device according to claim 18,
wherein the inhaler has:
a first container connected to the inhalation port and storing liquid inhaled from the inhalation port;
a second container connected to the first container and passing gas and prevents liquid from passing; and
a third container connected to the second container and the suction hole of the pump, and adjusting a suction pressure of the gas sucked by the pump.

* * * * *